United States Patent [19]
Chen et al.

[11] Patent Number: 5,889,159
[45] Date of Patent: Mar. 30, 1999

[54] MONOCLONAL ANTIBODIES TO TUMOR MARKER TC1 AND METHODS FOR USE OF SAME

[75] Inventors: Lan Bo Chen, Lexington, Mass.; Shideng Bao, Houston, Tex.; Yuan Liu, Lexington, Mass.

[73] Assignee: Dana-Farber Cancer Institute, Inc., Boston, Mass.

[21] Appl. No.: 448,388

[22] PCT Filed: Oct. 31, 1994

[86] PCT No.: PCT/US94/12502

§ 371 Date: May 28, 1996

§ 102(e) Date: May 28, 1996

[87] PCT Pub. No.: WO95/11923

PCT Pub. Date: May 4, 1995

Related U.S. Application Data

[62] Division of Ser. No. 146,488, Oct. 29, 1993, abandoned.

[51] Int. Cl.[6] .............................. C07K 16/30; C12N 5/12; G01N 33/53; G01N 33/577

[52] U.S. Cl. .................................. 530/388.8; 530/388.85; 530/387.7; 435/7.1; 435/7.2; 435/7.23; 435/330; 435/331

[58] Field of Search ............................. 530/388.2, 387.7, 530/388.8, 388.85; 435/7.1, 7.21, 7.23, 7.2, 330, 331

[56] References Cited

U.S. PATENT DOCUMENTS 5,348,874  9/1994  Savakis .

FOREIGN PATENT DOCUMENTS

0549107A1  6/1993  European Pat. Off. .
0562508A2  9/1993  European Pat. Off. .
WO9304198  3/1993  WIPO .
WO9318176  9/1993  WIPO .

OTHER PUBLICATIONS

Bao et al., "Identification and isolation of differentially expressed genes by palindromic PCT," *Molecular Biology of the Cell* 4:357A (1993).
Meyers et al., "Reverse Transcription and DNA Amplification by a *Thermus thermophilus* DNA Polymerase," *Biochemistry*, 30:7661–7666 (1991).
Liang et al., "Differential Display of Eukaryotic Messenger RNA by means of the Polymerase Chain Reaction," *Science*, 257:967–971 (1992).
Welsh et al., "Arbitrarily primed PCR fingerprinting of RNA," *Nucleic Acids Research*, 20:34965–4970 (1992).
Barnes et al., *Proc. Natl. Acad. Sci.* USA 87:6679–6683 (1990).
Mao et al., *J. Interferon Res.* 9:659–669 (1989).
Takeshita et al., *Biochem. J.* 294:271–278 (1993).
Skonier et al., *DNA Cell Biol.* 11:511–522 (1992).
Breant, Diabetologia 33:586, 1990.
McGowan, J. Biol Chem 266:4911 1991.

*Primary Examiner*—Toni R. Scheiner
*Assistant Examiner*—Nancy A. Johnson
*Attorney, Agent, or Firm*—Weingarten, Schurgin, Gagnebin & Hayes LLP

[57] ABSTRACT

The invention encompasses a novel tumor marker TC1 which is present on tumor cells and absent on corresponding normal cells, nucleic acid encoding the tumor marker, and monoclonal antibodies to tumor marker TC1.

9 Claims, 37 Drawing Sheets

```
  1/1
  CTG ATC CAT GGG AAC CAG ATT GCA ACA AAT GGT GTT GTC CAT GTC ATT GAC CGT GTG CTT
   L   I   H   G   N   Q   I   A   T   N   G   V   V   H   V   I   D   R   V   L
                                                 31/11
 61/21
 ACA CAA ATT GGT ACC ATT TCA ATT CAA GAC TTC ATT GAA GCA GAA GAT GAC CTT TCA TCT TTT
  T   Q   I   G   T   I   S   I   Q   D   F   I   E   A   E   D   D   L   S   S   F
 121/41                                          91/31
 AGA GCA GCT GCC ATC ACA TCG GAC ATA TTG GAG GCC CTT GGA AGA GAC GGT CAC TTC ACA
  R   A   A   A   I   T   S   D   I   L   E   A   L   G   R   D   G   H   F   T
 181/61                                         151/51
 CTC TTT GCT CCC AAT GAG GCT TTT GAG AAA CTT CCA CGA GGT GTC CTA GAA AGG ATC
  L   F   A   P   N   E   A   F   E   K   L   P   R   G   V   L   E   R   I
 241/81                                         211/71
 ATG GGA GAC AAA GTG TCC GAA GCT CTT ATG AAG TAC CAC ATC TTA AAT ACT CTC CAG
  M   G   D   K   V   S   E   A   L   M   K   Y   H   I   L   N   T   L   Q
 301/101                                        271/91
 TGT TCT GAG TCT ATT ATG GGA GGA GCA GTC TTT GAG ACG CTG GAA GGA AAT ACA ATT GAG
  C   S   E   S   I   M   G   G   A   V   F   E   T   L   E   G   N   T   I   E
 361/121                                        331/111
 ATA GGA TGT GAC GGT GAC AGT ATA ACA GTA AAT GGA ATC AAA ATG GTG CTA ATT AAG GAT
  I   G   C   D   G   D   S   I   T   V   N   G   I   K   M   V   L   I   K   D
 421/141                                        391/131
 ATT GTG ACA AAT GGT AAT GTG ATC GTG GCT GGA CAG CAT TTG ATT GAT CAG GTC ATT CCT GAT CTT GTG GCC CAA
  I   V   T   N   G   N   V   I   V   A   G   Q   H   L   I   D   Q   V   I   P   D   L   V   A   Q
 481/161                                        451/151
 AAA CAA GTT GAG ATT GCT CTG AGG CCA GAT GGA GAA TAC ACT TTC ACG GAT CTT GTG GCC CAA
  K   Q   V   E   I   A   L   R   P   D   G   E   Y   T   F   T   D   L   V   A   Q
 541/181                                        511/171
 TTA GGC TTG GCA TCT GCT CTG AGG CCA GAT GGA GAA TAC ACT TTG CTG GCA CCT GTG AAT
  L   G   L   A   S   A   L   R   P   D   G   E   Y   T   L   L   A   P   V   N
 601/201                                        571/191
 AAT GCA TTT TCT GAT GAT ACT CTC AGC ATG GAT CAG
  N   A   F   S   D   D   T   L   S   M   D   Q
                                                631/211
```

FIG. 3

TC1-DNA -> Genes

DNA Sequence   3126 b.p.   gccaccatgtag...ctttctcgtgcc   linear

```
  1 gccaccatgtagcccgcgtcaccgttctgcattccgcagc ATG GCT CTG CCT GCC CGA ATC CTC GCT
  1                                           M   A   L   P   A   R   I   L   A 70 CTG GCC CTC GCA CTG GCG CTC GGA CCC GCC GTG ACA CTG GCC AAC CCG AGA ACG CCG
 10  L   A   L   A   L   A   L   G   P   A   V   T   L   A   N   P   R   T   P 130 TAC GAG CTG GTA CTC CAG AAG AGC TCG GCA CGA GGG GGT GCA CGG GAC CAA GGC CCA AAT GTC
 30  Y   E   L   V   L   Q   K   S   S   A   R   G   G   A   R   D   Q   G   P   N   V 190 TGT GCC CTT CAA CAG ATT TTG GGC ACC AAA AAG ACT GTG TAC TTC AGC ACT TGT AAG AAC TGG
 50  C   A   L   Q   Q   I   L   G   T   K   K   T   V   Y   F   S   T   C   K   N   W 250 TAT AAA AAG TCC ATC TGT GGA CAG AAA ACG TTA TAT GAA TGT TGC CCT GGT TAT
 70  Y   K   K   S   I   C   G   Q   K   T   L   Y   E   C   C   P   G   Y 310 ATG AGA ATG GAA GGA ATG AAA GGC TGC CCA GCA GTT TTG CCC ATT GAC CAT GTT TAT GGC
 90  M   R   M   E   G   M   K   G   C   P   A   V   L   P   I   D   H   V   Y   G 370 ACT CTG GGC ATC GTG GGA GAA GCC ACA ACG CAG CGC TAT TCT GAC GCC TCA AAA CTG AGG
110  T   L   G   I   V   G   E   A   T   T   Q   R   Y   S   D   A   S   K   L   R 430 GAG GAG ATC GAG GGA AAG GGA TCC AGA GGT TTG GAG AGC TAT TCT GCA CCG AGT AAT GAG GCT TGG GAC
130  E   E   I   E   G   K   G   S   R   G   L   E   S   Y   F   A   P   S   N   E   A   W   D 490 AAC TTG GAT TCT GAT ATC CGT AAT AAG AGA ATG TTG GAG AGC AAC GTG AAT GTT GAA TTA CTG AAT
150  N   L   D   S   D   I   R   N   K   R   M   L   E   S   N   V   N   V   E   L   L   N 550 GCT TTA CAT AGT CAT CAC ATG ATT AAT AAG AGA ATG TTG ACC AAG GAC TTA AAA AAT GGC ATG
170  A   L   H   S   H   H   M   I   N   K   R   M   L   T   K   D   L   K   N   G   M
```

FIG. 4A

| | | | | | | | | | | | | | | | | | | |
|---|---|---|---|---|---|---|---|---|---|---|---|---|---|---|---|---|---|---|
| 610 | ATT | ATT | CCT | TCA | ATG | TAT | AAC | AAT | TTG | GGG | CTT | TTC | ATT | AAC | CAT | TAT | CCT | AAT | GGG | GTT |
| 190 | I | I | P | S | M | Y | N | N | L | G | L | F | I | N | H | Y | P | N | G | V |
| 670 | GTC | ACT | GTT | AAT | TGT | GCT | CGA | ATC | ATC | CAT | GGG | AAC | CAG | ATT | AAC | ACA | AAT | GGT | GAA | GCA |
| 210 | V | T | V | N | C | A | R | I | I | H | G | N | Q | I | N | T | N | G | E | A |
| 730 | CAT | GTC | ATT | GAC | CGT | GTG | CTT | ACA | CAA | ATT | GGT | GCC | ATC | ACC | TCA | ATT | GAC | TTC | ATT | GAA |
| 230 | H | V | I | D | R | V | L | T | Q | I | G | A | I | T | S | I | D | F | I | E |
| 790 | GAA | GAT | GAC | CTT | TCA | TCT | TTT | AGA | GCA | GCT | GCC | ATC | CCC | ACC | ACA | TCG | GAC | ATA | TTG | GAG |
| 250 | E | D | D | L | S | S | F | R | A | A | A | I | P | T | T | S | D | I | L | E |
| 850 | GGA | AGA | GAC | GGT | CAC | TTC | ACA | AGG | ATC | CTC | TTT | GCT | CCC | AAA | GTG | GCT | GAG | GCT | TTT | GAG |
| 270 | G | R | D | G | H | F | T | R | I | L | F | A | P | K | V | A | E | A | F | E |
| 910 | CGA | GGT | GTC | CTA | GAA | AGG | ATG | ATG | TGT | GAC | GGT | GAC | AAT | GGG | GCA | GCA | GTC | TTT | GAG | ACG |
| 290 | R | G | V | L | E | R | M | M | C | D | G | D | N | G | A | A | V | F | E | T |
| 970 | CAC | ATC | TTA | AAT | ACT | CTC | CAG | ATA | GAG | TCT | ATT | GTG | AAT | GGT | AGT | ATA | ACA | GTA | AAT | GGA |
| 310 | H | I | L | N | T | L | Q | I | E | S | I | V | N | G | S | I | T | V | N | G |
| 1030 | CTG | GAA | GGA | AAT | ACA | ATT | GAG | GAT | TCT | GCC | AAA | GTT | CAA | CAA | GTT | ATT | GAG | CTG | GCT | CAT |
| 330 | L | E | G | N | T | I | E | D | S | A | K | V | Q | Q | V | I | E | L | A | H |
| 1090 | AAA | ATG | GTG | AAA | AAG | GAT | TCT | GCC | AAA | GTT | CAA | CAA | GTT | ATT | GAG | CTG | GCT | CAT | TTG | CAT |
| 350 | K | M | V | K | K | D | S | A | K | V | Q | Q | V | I | E | L | A | H | L | H |
| 1150 | GTC | CTA | ATT | CCT | GAT | CTT | GTG | GCC | CAA | TTA | GGC | TTG | GCA | TCT | GCT | CTG | AGG | CCA | AAA | CAG |
| 370 | V | L | I | P | D | L | V | A | Q | L | G | L | A | S | A | L | R | P | K | Q |
| 1210 | TTC | ACG | GAT | CTT | GTG | GCC | CAA | TTA | GGC | TTG | GCA | TCT | GCT | CTG | AGG | CCA | AAA | CAG | GAT | GGA |
| 390 | F | T | D | L | V | A | Q | L | G | L | A | S | A | L | R | P | K | Q | D | G |
| 1270 | ACT | TTG | CTG | GCA | CCT | GTG | AAT | GCA | TTT | TCT | GAT | GAT | ACT | CTC | AGC | ATG | GAT | CAG | GAA | TAC |
| 410 | T | L | L | A | P | V | N | A | F | S | D | D | T | L | S | M | D | Q | E | Y |

Four Repeats of TCI Protein

FIG. 5

Homology Between TC1 and Bigh3

```
TC1    1  M A L P A R I L A L A L A L P P A V T L A N P A R T P Y E L
Bigh3  1  M A L F V R L L A L A L A L G P A A T L A G P A K S P Y Q L V L Q K S A R G G R D Q G P N V C A L Q Q I L G T K K K Y F S
          V L Q H S R L R G . R Q H G P N V C A V T K V I G T N R K Y F T T C K N W Y K K S I C G Q K T V L Y E C C P G Y M R M E G M K
          N C K Q W Y Q R K I C G K S T V I S Y E C C P G Y E K V P G E K G C P A V L P I D H V Y G T L G I V G A T T Q R Y S D A S . K
          G C P A A L P L S N L Y E T L G V V G S T T T Q L Y T D R T E K L R E I E G K G S F T Y F A P S N E A W D N L D S D I R R G L
          L R P E M E G P G S F T I F A P S N E A W A S L P A E V L D S L E S N V N V E L L N A L H S H M I N K R M L T K D L K N G M I I
          V S N V N I E L L N A L R Y H M V G R R V L T D E L K H G M T L P S M Y N N L G L F I N H Y P N G V V T V N C A R I I H G N Q I
          T S M Y Q N S N I Q I H H Y P N G I V T V N C A R L L K A D H H A T N G V V H V I D R V L T Q I G T S I Q D F I E A E D D L S S
          A T N G V V H L I D K V I S T I T N N I Q Q I I E I E D T F E T F R A A I T S D I L E A L G R D G H F T L F A P T N E A F E K
          L R A A V A A S G L N T M L E G N G Q Y T L L A P T N E A F E K L P R G V L E R I M G D K V A S E A L M K Y H I L N T L Q C S E
          I P S E T L N R I L G D P E A L R D L L N N H I L K S A M C A E S I M G A V F E T L E G N T I E I G C D G D S I T V N G I K M
          A I V A G L S V E T L E G T T L E V G C S G D M L T I N G K A I V N K D I V T N N G V I H L I D Q V L I P D S A K Q V I E L A
          I S N K D I L A T N G V I H Y I D E L L I P D S A K T L F E L A G K Q Q T . T F T D L V A Q L G L A S A L R P D G E Y T L L A P
          A E S D V S T A I D L F R Q A G L G N H L S G S E R L T L L A P V N A F S D D T L S M D Q R L L K L I L Q N H I L K V K V G L
          L N S V F K D G T P P I D A H T R N L . L R N H I I K D Q L A S N E L Y N G Q I L E T I G G K Q L R V F V Y R T A V C I E N S C
          K Y L Y H G Q T L E T L G G K K L R V F V Y R N S L C I E N S C M E K G S K Q G R N G A I H I F R E I I K P A E K S L H E K L K
          I A A H D K R G R Y G T L F T M D R V L T P M G T V M D V L K Q D K R F T T F L S L L E A A D . . . . L K E L L T Q P G D W T
          G D N R F . . . . S M L V A A I Q S A G L T E T L N R E G V Y T
```

Homology Between TC1 and Fasciclin I

```
TC1 503 A E K S L H E K L K Q D K R F T T F L S L L E A A D L
GrF  26 G E K S L E Y K I R D D P D L S Q F Y S W L E H N E V
DrF  19 A A A D L A D K L R D D S E L S Q F Y S L L E S N Q I

TC1     K E L L T Q P G D W T L F V P T N D A F . . . K G M T
GrF     A N S T L Q L R Q V T V F A P T N L A F Q N Y K A R D
DrF     A N S T L S L R S C T I F V P T N E A F Q R Y K . . .

TC1     S E K E I L I R D K N A L Q N I I L Y H L T P G V F
GrF     G D E N I I L Y H M T N L A H S . . L D Q L G H K V L
DrF     S K T A H V L Y H I T T E A Y T . . Q K R L P N T V S

TC1     I G K . G F E P G V T N I L K T T Q G . S K I F L K E
GrF     S E L D G N P P . . . . L W I T R R R D T I F . . .
DrF     S D M A G N P P . . L Y I T K N S N G . . D I F . . .

TC1     V N D . T L L V N E L K S K E S D I M . T T N G V I H
GrF     V N N A R V L T . E R S N Y E A V N R H G K K Q V L H
DrF     V G N A R I I P . S L S V . E T N S D . G K R Q I M H

TC1     V V D K L L Y P A D . T P . V G . . . N D Q L L E I L
GrF     V V D S V L E P V W S T S . . G Q L Y N P D A F Q F L
DrF     I I D E V L E P L . . T V K A G H S D T P N N P . . .

TC1     N K L I K Y I Q I K F V R G S T F K E I P V T V Y R P
GrF     N Q . S E N L D L G L H R V R S F R Q R . V F Q . N Q
DrF     N A L . K F . . L K N A E E F N V D N I G V R T Y R S

TC1     T L T K V K I E G E P E F R L I K E G E T I T E V I H
GrF     K Q N D F K L E G K H T F . F I P V D E G F K P L P R
DrF     Q V T M A K K E S V Y D A A G Q H T F L V P V D E G F

TC1     G E P I K K                                      706
GrF     P E K I D Q K                                    221
DrF     K L S A R S S                                    211
```

FIG. 9

1. HT29 CELL  3. HT29 TUMOR
2. CX-1 CELL  4. CX-1 TUMOR

1, JMN; 2, JMN1B

1, JMN; 2, JMN1B

Nucleotide Sequence and Deduced Amino Acid Sequence of TC1

```
  1 attcgacgtctcgtccacaacagaactgcaacggagagactcaag ATG ATT CCC TTT TTA CCC ATG TTT   69
  1                                                M   I   P   F   L   P   M   F     8

70 TCT CTA CTA TTG CTG CTT ATT GTT AAC CCT ATA AAC GCC AAC AAT CAT TAT GAC AAG ATC  129
  9  S   L   L   L   L   L   I   V   N   P   I   N   A   N   N   H   Y   D   K   I   28

130 TTG GCT CAT AGT CGT ATC AGG GGT CGG GAC CAA GGC CCA AAT GTC TGT GCC CTT CAA CAG  189
 29  L   A   H   S   R   I   R   G   R   D   Q   G   P   N   V   C   A   L   Q   Q   48

190 ATT TTG GGC ACC AAA AAG TAC TTC AGC ACT TGT AAG AAC TGG TAT AAA AAG TCC ATC      249
 49  I   L   G   T   K   K   Y   F   S   T   C   K   N   W   Y   K   K   S   I       68

250 TGT GGA CAG AAA ACG ACT GTG TTA TAT GAA TGT TGC CCT GGT TAT ATG AGA ATG GAA GGA  309
 69  C   G   Q   K   T   T   V   L   Y   E   C   C   P   G   Y   M   R   M   E   G   88

310 ATG AAA GGC TGC CCA GCA GTT TTG CCC ATT GAC CAT GTT AAA CTG AGG GAG ATC GTG      369
 89  M   K   G   C   P   A   V   L   P   I   D   H   V   K   L   R   E   I   V      108

370 GGA GCC ACC ACA ACG CAG CGC TAT TCT GAC GCC TCA AAT GAG GCT TGG GAC AAC TTG GAT TCT GAT  429
109  G   A   T   T   T   Q   R   Y   S   D   A   S   N   E   A   W   D   N   L   D   S   D  128

430 AAG GGA TCC TTC ACT TAC TTT GCA CCG AGT AGC AGT GTT GAA TTA AAA AAT GGC ATG ATT CCT TCA ATG  489
129  K   G   S   F   T   Y   F   A   P   S   S   S   V   E   L   K   N   G   M   I   P   S   M  148

490 ATC CGT AGA GGT TTG GAG AGC AAC GTG AAC GTT GAA TTA CTG AAT GCT TTA CAT AGT CAT CAC  549
149  I   R   R   G   L   E   S   N   V   N   V   E   L   L   N   A   L   H   S   H  168

550 ATG ATT AAT AAG AGA ATG TTG ACC AAG GAC TTA AAA AAT CAT TAT AAC ATG ATT CCT TCA ATG  609
169  M   I   N   K   R   M   L   T   K   D   L   K   N   H   Y   N   M   I   P   S   M  188

610 TAT AAC AAT TTG GGG CTT TTC ATT AAC CAT TAT CCT AAT GGG GTT GTC ACT GTT AAT TGT  669
189  Y   N   N   L   G   L   F   I   N   H   Y   P   N   G   V   V   T   V   N   C  208
```

FIG. 28A

```
 670 GCT CGA ATC ATC CAT GGG AAC CAG ATT GCA ACA AAT GGT GTT CAT GTC ATT GAC CGT  729
 209  A   R   I   I   H   G   N   Q   I   A   T   N   G   V   H   V   I   D   R   228

730 GTG CTT ACA CAA ATT GGT ACC TCA ATT CAA GAC TTC ATT GAA GCA GAA GAT GAC CTT TCA  789
 229  V   L   T   Q   I   G   T   S   I   Q   D   F   I   E   A   E   D   D   L   S   248

790 TCT TTT AGA GCA GCT GCC ATC ACA GAC ATA TTG GAG GCC CTT GGA AGA GAC GGT CAC  849
 249  S   F   R   A   A   A   I   T   D   I   L   E   A   L   G   R   D   G   H   268

850 TTC ACA CTC TTT GCT CCC ACC AAT GAG TTT GAG AAA CTT CCA CGA GGT GTC CTA GAA  909
 269  F   T   L   F   A   P   T   N   E   F   E   K   L   P   R   G   V   L   E   288

910 AGG ATC ATG GGA GAC AAA GTG GCT TCC GAA GCT CTT ATG AAG TAC CAC ATC TTA AAT ACT  969
 289  R   I   M   G   D   K   V   A   S   E   A   L   M   K   Y   H   I   L   N   T   308

970 CTC CAG TGT TCT GAG TCT ATT ATG GGA GGA GCA GTC TTT GAG ACG CTG GAA GGA AAT ACA 1029
 309  L   Q   C   S   E   S   I   M   G   G   A   V   F   E   T   L   E   G   N   T   328

1030 ATT GAG ATA GGA TGT GAC GGT GAC AGT ATA ACA GTA AAT GGA ATC AAA ATG GTG AAC AAA 1089
 329  I   E   I   G   C   D   G   D   S   I   T   V   N   G   I   K   M   V   N   K   348

1090 AAG GAT ATT GTG ACA CAA GTT ATT GAG CTG GTG ATC CAT TTG ATT GAT CAG ACC TTC ACG GAT 1149
 349  K   D   I   V   T   Q   V   I   E   L   V   I   H   L   I   D   Q   T   F   T   D  368

1150 TCT GCC AAA CAA TTA GGC TTG GCA TCT GCT CTT CGG CCA AGG ACC CTC ACC TTC ACT TTG CTG GCA CCT 1209
 369  S   A   K   Q   L   G   L   A   S   A   L   R   P   R   T   L   T   F   T   L   L   A   P  388

1210 GCC CAA TTA AAT GCA TTT TCT GAT GAT ACT CTC AGC ATG GAT CAG CGC CTC CTT AAA TTA ATT 1269
 389  A   Q   L   N   A   F   S   D   D   T   L   S   M   D   Q   R   L   L   K   L   I   408

1270 GTG AAT GCA TTT TCT GAT GAT ACT CTC AGC ATG GAT CAG CGC CTC CTT AAA TTA ATT 1329
 409  V   N   A   F   S   D   D   T   L   S   M   D   Q   R   L   L   K   L   I   428

1330 CTG CAG AAT CAC ATA TTG AAA GTA AAA GTT GGC CTT AAT GAG CTT TAC AAC GGG CAA ATA 1389
 429  L   Q   N   H   I   L   K   V   K   V   G   L   N   E   L   Y   N   G   Q   I   448
```

FIG. 28B

```
1390 CTG GAA ACC ATC GGA GGC AAA CAG CTC AGA GTC TTC GTA TAT CGT ACA GCT GTC TGC ATT 1449
 449  L   E   T   I   G   G   K   Q   L   R   V   F   V   Y   R   T   A   V   C   I   468

1450 GAA AAT TCA TGC ATG GAG AAA GGG AGT AAG CAA GGG AGA AAC GGT GCG ATT CAC ATA TTC 1509
 469  E   N   S   C   M   E   K   G   S   K   Q   G   R   N   G   A   I   H   I   F   488

1510 CGC GAG ATC AAG CCA GCA GAG AAA TCC CTC CAT GAA AAG TTA AAA CAA GAT AAG CGC 1569
 489  R   E   I   K   P   A   E   K   S   L   H   E   K   L   K   Q   D   K   R   508

1570 TTT ACC TTC CTC AGC CTA CTT GAA GCT GCA GAC TTG AAA GAG CTC CTG ACA CAA CCT 1629
 509  F   T   F   L   S   L   L   E   A   A   D   L   K   E   L   L   T   Q   P   528

1630 GGA GAC TGG ACA TTA TTT GTG CCA ACC AAT GAT GCT TTT AAG GGA ATG ACT AGT GAA GAA 1689
 529  G   D   W   T   L   F   V   P   T   N   D   A   F   K   G   M   T   S   E   E   548

1690 AAA GAA ATT CTG ATA CGG GAC AAA GAT AAG CTT CAA AAC ATC ATT TAT CAC CTG ACA 1749
 549  K   E   I   L   I   R   D   K   D   K   L   Q   N   I   I   Y   H   L   T   568

1750 CCA GGA GTT TTC ATT GGA AAA TCT GAC ATG ACA ACA ACT GGT GTT ACT ATT CAT GTT 1809
 569  P   G   V   F   I   G   K   S   D   M   T   T   T   G   V   T   I   H   V   588

1810 CAA GGA AGC AAA ATT TTT CTG AAA GAA GTA AAT GAT ACA CTG CTT GAA ATA TTA AAT 1869
 589  Q   G   S   K   I   F   L   K   E   V   N   D   T   L   L   E   I   L   N   608

1870 TCA AAA GAA TCT GAC ATC ATG ACA ACA AAT GGT CAA CTG CTT CAT GAA ATA TTA AAT 1929
 609  S   K   E   S   D   I   M   T   T   N   G   Q   L   L   H   E   I   L   N   628

1930 TAT CCA GCA GAC ACA CCT GTT GGA ATT GAT CAA CTG CTG GAA ATA CTT AAT AAA TTA 1989
 629  Y   P   A   D   T   P   V   G   I   D   Q   L   L   E   I   L   N   K   L   648

1990 AAA TAC CAA ATT AAG TTT GTT CGT GGT AGC ACC TTC AAA GAA ATC CCC GTG ACT GTC 2049
 649  K   Y   Q   I   K   F   V   R   G   S   T   F   K   E   I   P   V   T   V   668

2050 TAT AGA CCC ACA CTA ACA AAA GTC AAA ATT GAA GGT GAA CCT GAA TTC AGA CTG ATT AAA 2109
 669  Y   R   P   T   L   T   K   V   K   I   E   G   E   P   E   F   R   L   I   K   688
```

FIG. 28C

```
2110 GAA GGT GAA ACA ATA ACT GAA GTG ATC CAT GGA GAG CCA ATT ATT AAA AAA TAC ACC AAA  2169
 689  E   G   E   T   I   T   E   V   I   H   G   E   P   I   I   K   K   Y   T   K    708

2170 ATC ATT GAT GGA GTG CCT GTG GAA ATA ACT GAA AAA GAG ACA CGA GAA GAA CGA ATC ATT  2229
 709  I   I   D   G   V   P   V   E   I   T   E   K   E   T   R   E   E   R   I   I    728

2230 ACA GGT CCT GAA ATA AAA TAC ACT AGG ATT TCT ACT GGA GGT GAA ACA GAA GAA ACT    2289
 729  T   G   P   E   I   K   Y   T   R   I   S   T   G   G   E   T   E   E   T        748

2290 CTG AAG AAA TTG TTA CAA GAA GAG GTC ACC AAG GTC ACC AAA TTC ATT GAA GGT GGT GAT  2349
 749  L   K   K   L   L   Q   E   E   V   T   K   V   T   K   F   I   E   G   G   D    768

2350 GGT CAT TTA TTT GAA GAT GAA GAA ATT AAA AGA CTG CTT CAG GAC ACA CCC GTG AGG      2409
 769  G   H   L   F   E   D   E   E   I   K   R   L   L   Q   D   T   P   V   R        788

2410 AAG TTG CAA GCC AAC AAA AAA AGT TCA AGG ATC TAG aagacgattaaggaaggtcgttctcagtgaa  2477
 789  K   L   Q   A   N   K   K   S   S   R   I   *                                    800

2478 aatccaaaaaccagaaaaatgttatacaacctaagtcaataacctgacctagaaattgtgagagccaagttgac        2557

2558 ttcaggaactgaaacatcagcacacaagaagcaatcatcaaatatctgaacacacaaattaatatattttttctgaatg   2637

2638 agaaacatgagggaaattgtggagtttagcctcctgtgtggtaaaggaattgaagaaaatataacacctacacccttttca 2717

2718 tcttgacattaaaagtttctggctaacttggaatccattgagagaaaatcctgtcaccagattcattacaattcaaatc   2797

2798 gaagagttgtgaactgtgttatcccattgaaaagaccgagccttgtatgtatggatacataaatgcacgcaagcca      2877

2878 ttatctctcccatgggaagctaagttatataaaatagtgctggtgtacaaactttatgatcaaaggctttgcacat      2957

2958 ttctatatgagtgggtttactggtaaatatgttatttttacaactaatttgtactctcagaatgtttgtcatatgct     3037

3038 tcttgcaatgcatattttttaatctcaaacgtttcaataaaccattttcagatataaagagaattacttcaaattgag    3117

3118 taattcagaaaactcaagattaagtgtttggacttgggaataggacttatacctcttttctcgtgcc               3195
```

FIG. 28D 5,889,159

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 636 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..636

( x i ) SEQUENCE DESCRIPTION: SEQ ID NO:1:

```
CTG  ATC  CAT  GGG  AAC  CAG  ATT  GCA  ACA  AAT  GGT  GTT  GTC  CAT  GTC  ATT        48
Leu  Ile  His  Gly  Asn  Gln  Ile  Ala  Thr  Asn  Gly  Val  Val  His  Val  Ile
 1              5                        10                       15

GAC  CGT  GTG  CTT  ACA  CAA  ATT  GGT  ACC  TCA  ATT  CAA  GAC  TTC  ATT  GAA        96
Asp  Arg  Val  Leu  Thr  Gln  Ile  Gly  Thr  Ser  Ile  Gln  Asp  Phe  Ile  Glu
               20                       25                       30

GCA  GAA  GAT  GAC  CTT  TCA  TCT  TTT  AGA  GCA  GCT  GCC  ATC  ACA  TCG  GAC       144
Ala  Glu  Asp  Asp  Leu  Ser  Ser  Phe  Arg  Ala  Ala  Ala  Ile  Thr  Ser  Asp
                35                       40                       45

ATA  TTG  GAG  GCC  CTT  GGA  AGA  GAC  GGT  CAC  TTC  ACA  CTC  TTT  GCT  CCC       192
Ile  Leu  Glu  Ala  Leu  Gly  Arg  Asp  Gly  His  Phe  Thr  Leu  Phe  Ala  Pro
     50                       55                       60

ACC  AAT  GAG  GCT  TTT  GAG  AAA  CTT  CCA  CGA  GGT  GTC  CTA  GAA  AGG  ATC       240
Thr  Asn  Glu  Ala  Phe  Glu  Lys  Leu  Pro  Arg  Gly  Val  Leu  Glu  Arg  Ile
 65                       70                       75                       80

ATG  GGA  GAC  AAA  GTG  GCT  TCC  GAA  GCT  CTT  ATG  AAG  TAC  CAC  ATC  TTA       288
Met  Gly  Asp  Lys  Val  Ala  Ser  Glu  Ala  Leu  Met  Lys  Tyr  His  Ile  Leu
                85                       90                       95

AAT  ACT  CTC  CAG  TGT  TCT  GAG  TCT  ATT  ATG  GGA  GGA  GCA  GTC  TTT  GAG       336
Asn  Thr  Leu  Gln  Cys  Ser  Glu  Ser  Ile  Met  Gly  Gly  Ala  Val  Phe  Glu
               100                      105                      110

ACG  CTG  GAA  GGA  AAT  ACA  ATT  GAG  ATA  GGA  TGT  GAC  GGT  GAC  AGT  ATA       384
Thr  Leu  Glu  Gly  Asn  Thr  Ile  Glu  Ile  Gly  Cys  Asp  Gly  Asp  Ser  Ile
          115                      120                      125

ACA  GTA  AAT  GGA  ATC  AAA  ATG  GTG  AAC  AAA  AAG  GAT  ATT  GTG  ACA  AAT       432
Thr  Val  Asn  Gly  Ile  Lys  Met  Val  Asn  Lys  Lys  Asp  Ile  Val  Thr  Asn
     130                      135                      140

AAT  GGT  GTG  ATC  CAT  TTG  ATT  GAT  CAG  GTC  CTA  ATT  CCT  GAT  TCT  GCC       480
Asn  Gly  Val  Ile  His  Leu  Ile  Asp  Gln  Val  Leu  Ile  Pro  Asp  Ser  Ala
145                      150                      155                      160

AAA  CAA  GTT  ATT  GAG  CTG  GCT  GGA  AAA  CAG  CAA  ACC  ACC  TTC  ACG  GAT       528
Lys  Gln  Val  Ile  Glu  Leu  Ala  Gly  Lys  Gln  Gln  Thr  Thr  Phe  Thr  Asp
               165                      170                      175

CTT  GTG  GCC  CAA  TTA  GGC  TTG  GCA  TCT  GCT  CTG  AGG  CCA  GAT  GGA  GAA       576
Leu  Val  Ala  Gln  Leu  Gly  Leu  Ala  Ser  Ala  Leu  Arg  Pro  Asp  Gly  Glu
                    180                      185                      190

TAC  ACT  TTG  CTG  GCA  CCT  GTG  AAT  AAT  GCA  TTT  TCT  GAT  GAT  ACT  CTC       624
Tyr  Thr  Leu  Leu  Ala  Pro  Val  Asn  Asn  Ala  Phe  Ser  Asp  Asp  Thr  Leu
               195                      200                      205
```

| AGC ATG GAT CAG | 636 |
|---|---|
| Ser Met Asp Gln |  |
| 210 |  |

(2) INFORMATION FOR SEQ ID NO:2:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Ile His Gly Asn Gln Ile Ala Thr Asn Gly Val Val His Val Ile
 1               5                  10                  15
Asp Arg Val Leu Thr Gln Ile Gly Thr Ser Ile Gln Asp Phe Ile Glu
            20                  25                  30
Ala Glu Asp Asp Leu Ser Ser Phe Arg Ala Ala Ala Ile Thr Ser Asp
        35                  40                  45
Ile Leu Glu Ala Leu Gly Arg Asp Gly His Phe Thr Leu Phe Ala Pro
    50                  55                  60
Thr Asn Glu Ala Phe Glu Lys Leu Pro Arg Gly Val Leu Glu Arg Ile
65                  70                  75                  80
Met Gly Asp Lys Val Ala Ser Glu Ala Leu Met Lys Tyr His Ile Leu
                85                  90                  95
Asn Thr Leu Gln Cys Ser Glu Ser Ile Met Gly Gly Ala Val Phe Glu
            100                 105                 110
Thr Leu Glu Gly Asn Thr Ile Glu Ile Gly Cys Asp Gly Asp Ser Ile
        115                 120                 125
Thr Val Asn Gly Ile Lys Met Val Asn Lys Lys Asp Ile Val Thr Asn
    130                 135                 140
Asn Gly Val Ile His Leu Ile Asp Gln Val Leu Ile Pro Asp Ser Ala
145                 150                 155                 160
Lys Gln Val Ile Glu Leu Ala Gly Lys Gln Gln Thr Thr Phe Thr Asp
                165                 170                 175
Leu Val Ala Gln Leu Gly Leu Ala Ser Ala Leu Arg Pro Asp Gly Glu
            180                 185                 190
Tyr Thr Leu Leu Ala Pro Val Asn Asn Ala Phe Ser Asp Asp Thr Leu
        195                 200                 205
Ser Met Asp Gln
    210
```

(2) INFORMATION FOR SEQ ID NO:3:

(i) SEQUENCE CHARACTERISTICS:
        (A) LENGTH: 3126 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 43..2376

(xi) SEQUENCE DESCRIPTION: SEQ ID NO:3:

| GCCACCATGT AGCCCGCGTC ACCGTTCTGC GCATTCCGCA GC ATG GCT CTG CCT | 54 |
|---|---|

|  |  |  |  |  |  |  |  |  |  |  |  |  |  |  | Met | Ala | Leu | Pro |  |
|--|--|--|--|--|--|--|--|--|--|--|--|--|--|--|--|--|--|--|--|
|  |  |  |  |  |  |  |  |  |  |  |  |  |  |  |  |  | 1 |  |  |

```
GCC  CGA  ATC  CTC  GCT  CTG  GCC  CTC  GCA  CTG  GCG  CTC  GGA  CCC  GCC  GTG                    102
Ala  Arg  Ile  Leu  Ala  Leu  Ala  Leu  Ala  Leu  Ala  Leu  Gly  Pro  Ala  Val
     5                   10                  15                            20

ACA  CTG  GCC  AAC  CCG  GCG  AGA  ACG  CCG  TAC  GAG  CTG  GTA  CTC  CAG  AAG                    150
Thr  Leu  Ala  Asn  Pro  Ala  Arg  Thr  Pro  Tyr  Glu  Leu  Val  Leu  Gln  Lys
                    25                  30                            35

AGC  TCG  GCA  CGA  GGG  GGT  CGG  GAC  CAA  GGC  CCA  AAT  GTC  TGT  GCC  CTT                    198
Ser  Ser  Ala  Arg  Gly  Gly  Arg  Asp  Gln  Gly  Pro  Asn  Val  Cys  Ala  Leu
               40                       45                       50

CAA  CAG  ATT  TTG  GGC  ACC  AAA  AAG  AAA  TAC  TTC  AGC  ACT  TGT  AAG  AAC                    246
Gln  Gln  Ile  Leu  Gly  Thr  Lys  Lys  Lys  Tyr  Phe  Ser  Thr  Cys  Lys  Asn
               55                       60                       65

TGG  TAT  AAA  AAG  TCC  ATC  TGT  GGA  CAG  AAA  ACG  ACT  GTG  TTA  TAT  GAA                    294
Trp  Tyr  Lys  Lys  Ser  Ile  Cys  Gly  Gln  Lys  Thr  Thr  Val  Leu  Tyr  Glu
          70                       75                  80

TGT  TGC  CCT  GGT  TAT  ATG  AGA  ATG  GAA  GGA  ATG  AAA  GGC  TGC  CCA  GCA                    342
Cys  Cys  Pro  Gly  Tyr  Met  Arg  Met  Glu  Gly  Met  Lys  Gly  Cys  Pro  Ala
85                       90                       95                      100

GTT  TTG  CCC  ATT  GAC  CAT  GTT  TAT  GGC  ACT  CTG  GGC  ATC  GTG  GGA  GCC                    390
Val  Leu  Pro  Ile  Asp  His  Val  Tyr  Gly  Thr  Leu  Gly  Ile  Val  Gly  Ala
                    105                 110                           115

ACC  ACA  ACG  CAG  CGC  TAT  TCT  GAC  GCC  TCA  AAA  CTG  AGG  GAG  GAG  ATC                    438
Thr  Thr  Thr  Gln  Arg  Tyr  Ser  Asp  Ala  Ser  Lys  Leu  Arg  Glu  Glu  Ile
               120                      125                      130

GAG  GGA  AAG  GGA  TCC  TTC  ACT  TAC  TTT  GCA  CCG  AGT  AAT  GAG  GCT  TGG                    486
Glu  Gly  Lys  Gly  Ser  Phe  Thr  Tyr  Phe  Ala  Pro  Ser  Asn  Glu  Ala  Trp
          135                      140                      145

GAC  AAC  TTG  GAT  TCT  GAT  ATC  CGT  AGA  GGT  TTG  GAG  AGC  AAC  GTG  AAT                    534
Asp  Asn  Leu  Asp  Ser  Asp  Ile  Arg  Arg  Gly  Leu  Glu  Ser  Asn  Val  Asn
     150                      155                      160

GTT  GAA  TTA  CTG  AAT  GCT  TTA  CAT  AGT  CAC  ATG  ATT  AAT  AAG  AGA  ATG                    582
Val  Glu  Leu  Leu  Asn  Ala  Leu  His  Ser  His  Met  Ile  Asn  Lys  Arg  Met
165                      170                      175                      180

TTG  ACC  AAG  GAC  TTA  AAA  AAT  GGC  ATG  ATT  ATT  CCT  TCA  ATG  TAT  AAC                    630
Leu  Thr  Lys  Asp  Leu  Lys  Asn  Gly  Met  Ile  Ile  Pro  Ser  Met  Tyr  Asn
               185                      190                      195

AAT  TTG  GGG  CTT  TTC  ATT  AAC  CAT  TAT  CCT  AAT  GGG  GTT  GTC  ACT  GTT                    678
Asn  Leu  Gly  Leu  Phe  Ile  Asn  His  Tyr  Pro  Asn  Gly  Val  Val  Thr  Val
          200                      205                           210

AAT  TGT  GCT  CGA  ATC  ATC  CAT  GGG  AAC  CAG  ATT  GCA  ACA  AAT  GGT  GTT                    726
Asn  Cys  Ala  Arg  Ile  Ile  His  Gly  Asn  Gln  Ile  Ala  Thr  Asn  Gly  Val
          215                      220                      225

GTC  CAT  GTC  ATT  GAC  CGT  GTG  CTT  ACA  CAA  ATT  GGT  ACC  TCA  ATT  CAA                    774
Val  His  Val  Ile  Asp  Arg  Val  Leu  Thr  Gln  Ile  Gly  Thr  Ser  Ile  Gln
     230                      235                      240

GAC  TTC  ATT  GAA  GCA  GAA  GAT  GAC  CTT  TCA  TCT  TTT  AGA  GCA  GCT  GCC                    822
Asp  Phe  Ile  Glu  Ala  Glu  Asp  Asp  Leu  Ser  Ser  Phe  Arg  Ala  Ala  Ala
245                      250                      255                      260

ATC  ACA  TCG  GAC  ATA  TTG  GAG  GCC  CTT  GGA  AGA  GAC  GGT  CAC  TTC  ACA                    870
Ile  Thr  Ser  Asp  Ile  Leu  Glu  Ala  Leu  Gly  Arg  Asp  Gly  His  Phe  Thr
                    265                      270                      275

CTC  TTT  GCT  CCC  ACC  AAT  GAG  GCT  TTT  GAG  AAA  CTT  CCA  CGA  GGT  GTC                    918
Leu  Phe  Ala  Pro  Thr  Asn  Glu  Ala  Phe  Glu  Lys  Leu  Pro  Arg  Gly  Val
               280                      285                      290

CTA  GAA  AGG  ATC  ATG  GGA  GAC  AAA  GTG  GCT  TCC  GAA  GCT  CTT  ATG  AAG                    966
Leu  Glu  Arg  Ile  Met  Gly  Asp  Lys  Val  Ala  Ser  Glu  Ala  Leu  Met  Lys
          295                      300                      305

TAC  CAC  ATC  TTA  AAT  ACT  CTC  CAG  TGT  TCT  GAG  TCT  ATT  ATG  GGA  GGA                   1014
```

```
Tyr His Ile Leu Asn Thr Leu Gln Cys Ser Glu Ser Ile Met Gly Gly
    310                 315                 320

GCA GTC TTT GAG ACG CTG GAA GGA AAT ACA ATT GAG ATA GGA TGT GAC        1062
Ala Val Phe Glu Thr Leu Glu Gly Asn Thr Ile Glu Ile Gly Cys Asp
325                 330                 335                 340

GGT GAC AGT ATA ACA GTA AAT GGA ATC AAA ATG GTG AAC AAA AAG GAT        1110
Gly Asp Ser Ile Thr Val Asn Gly Ile Lys Met Val Asn Lys Lys Asp
                345                 350                 355

ATT GTG ACA AAT AAT GGT GTG ATC CAT TTG ATT GAT CAG GTC CTA ATT        1158
Ile Val Thr Asn Asn Gly Val Ile His Leu Ile Asp Gln Val Leu Ile
            360                 365                 370

CCT GAT TCT GCC AAA CAA GTT ATT GAG CTG GCT GGA AAA CAG CAA ACC        1206
Pro Asp Ser Ala Lys Gln Val Ile Glu Leu Ala Gly Lys Gln Gln Thr
        375                 380                 385

ACC TTC ACG GAT CTT GTG GCC CAA TTA GGC TTG GCA TCT GCT CTG AGG        1254
Thr Phe Thr Asp Leu Val Ala Gln Leu Gly Leu Ala Ser Ala Leu Arg
    390                 395                 400

CCA GAT GGA GAA TAC ACT TTG CTG GCA CCT GTG AAT AAT GCA TTT TCT        1302
Pro Asp Gly Glu Tyr Thr Leu Leu Ala Pro Val Asn Asn Ala Phe Ser
405                 410                 415                 420

GAT GAT ACT CTC AGC ATG GAT CAG CGC CTC CTT AAA TTA ATT CTG CAG        1350
Asp Asp Thr Leu Ser Met Asp Gln Arg Leu Leu Lys Leu Ile Leu Gln
                425                 430                 435

AAT CAC ATA TTG AAA GTA AAA GTT GGC CTT AAT GAG CTT TAC AAC GGG        1398
Asn His Ile Leu Lys Val Lys Val Gly Leu Asn Glu Leu Tyr Asn Gly
            440                 445                 450

CAA ATA CTG GAA ACC ATC GGA GGC AAA CAG CTC AGA GTC TTC GTA TAT        1446
Gln Ile Leu Glu Thr Ile Gly Gly Lys Gln Leu Arg Val Phe Val Tyr
        455                 460                 465

CGT ACA GCT GTC TGC ATT GAA AAT TCA TGC ATG GAG AAA GGG AGT AAG        1494
Arg Thr Ala Val Cys Ile Glu Asn Ser Cys Met Glu Lys Gly Ser Lys
    470                 475                 480

CAA GGG AGA AAC GGT GCG ATT CAC ATA TTC CGC GAG ATC ATC AAG CCA        1542
Gln Gly Arg Asn Gly Ala Ile His Ile Phe Arg Glu Ile Ile Lys Pro
485                 490                 495                 500

GCA GAG AAA TCC CTC CAT GAA AAG TTA AAA CAA GAT AAG CGC TTT ACG        1590
Ala Glu Lys Ser Leu His Glu Lys Leu Lys Gln Asp Lys Arg Phe Thr
                505                 510                 515

ACC TTC CTC AGC CTA CTT GAA GCT GCA GAC TTG AAA GAG CTC CTG ACA        1638
Thr Phe Leu Ser Leu Leu Glu Ala Ala Asp Leu Lys Glu Leu Leu Thr
            520                 525                 530

CAA CCT GGA GAC TGG ACA TTA TTT GTG CCA ACC AAT GAT GCT TTT AAG        1686
Gln Pro Gly Asp Trp Thr Leu Phe Val Pro Thr Asn Asp Ala Phe Lys
        535                 540                 545

GGA ATG ACT AGT GAA GAA AAA GAA ATT CTG ATA CGG GAC AAA AAT GCT        1734
Gly Met Thr Ser Glu Glu Lys Glu Ile Leu Ile Arg Asp Lys Asn Ala
    550                 555                 560

CTT CAA AAC ATC ATT CTT TAT CAC CTG ACA CCA GGA GTT TTC ATT GGA        1782
Leu Gln Asn Ile Ile Leu Tyr His Leu Thr Pro Gly Val Phe Ile Gly
565                 570                 575                 580

AAA GGA TTT GAA CCT GGT GTT ACT AAC ATT TTA AAG ACC ACA CAA GGA        1830
Lys Gly Phe Glu Pro Gly Val Thr Asn Ile Leu Lys Thr Thr Gln Gly
                585                 590                 595

AGC AAA ATC TTT CTG AAA GAA GTA AAT GAT ACA CTT CTG GTG AAT GAA        1878
Ser Lys Ile Phe Leu Lys Glu Val Asn Asp Thr Leu Leu Val Asn Glu
            600                 605                 610

TTG AAA TCA AAA GAA TCT GAC ATC ATG ACA ACA AAT GGT GTA ATT CAT        1926
Leu Lys Ser Lys Glu Ser Asp Ile Met Thr Thr Asn Gly Val Ile His
        615                 620                 625

GTT GTA GAT AAA CTC CTC TAT CCA GCA GAC ACA CCT GTT GGA AAT GAT        1974
```

```
Val  Val  Asp  Lys  Leu  Leu  Tyr  Pro  Ala  Asp  Thr  Pro  Val  Gly  Asn  Asp
     630                      635                 640

CAA  CTG  CTG  GAA  ATA  CTT  AAT  AAA  TTA  ATC  AAA  TAC  ATC  CAA  ATT  AAG     2022
Gln  Leu  Leu  Glu  Ile  Leu  Asn  Lys  Leu  Ile  Lys  Tyr  Ile  Gln  Ile  Lys
645                      650                 655                      660

TTT  GTT  CGT  GGT  AGC  ACC  TTC  AAA  GAA  ATC  CCC  GTG  ACT  GTC  TAT  AGA     2070
Phe  Val  Arg  Gly  Ser  Thr  Phe  Lys  Glu  Ile  Pro  Val  Thr  Val  Tyr  Arg
                    665                 670                      675

CCC  ACA  CTA  ACA  AAA  GTC  AAA  ATT  GAA  GGT  GAA  CCT  GAA  TTC  AGA  CTG     2118
Pro  Thr  Leu  Thr  Lys  Val  Lys  Ile  Glu  Gly  Glu  Pro  Glu  Phe  Arg  Leu
               680                      685                      690

ATT  AAA  GAA  GGT  GAA  ACA  ATA  ACT  GAA  GTG  ATC  CAT  GGA  GAG  CCA  ATT     2166
Ile  Lys  Glu  Gly  Glu  Thr  Ile  Thr  Glu  Val  Ile  His  Gly  Glu  Pro  Ile
          695                      700                 705

ATT  AAA  AAA  TAC  ACC  AAA  ATC  ATT  GAT  GGA  GTG  CCT  GTG  GAA  ATA  ACT     2214
Ile  Lys  Lys  Tyr  Thr  Lys  Ile  Ile  Asp  Gly  Val  Pro  Val  Glu  Ile  Thr
     710                      715                 720

GAA  AAA  GAG  ACA  CGA  GAA  GAA  CGA  ATC  ATT  ACA  GGT  CCT  GAA  ATA  AAA     2262
Glu  Lys  Glu  Thr  Arg  Glu  Glu  Arg  Ile  Ile  Thr  Gly  Pro  Glu  Ile  Lys
725                 730                      735                      740

TAC  ACT  AGG  ATT  TCT  ACT  GGA  GGT  GGA  GAA  ACA  GAA  GAA  ACT  CTG  AAG     2310
Tyr  Thr  Arg  Ile  Ser  Thr  Gly  Gly  Gly  Glu  Thr  Glu  Glu  Thr  Leu  Lys
                    745                 750                      755

AAA  TTG  TTA  CAA  GAA  GAC  ACA  CCC  GTG  AGG  AAG  TTG  CAA  GCC  AAC  AAA     2358
Lys  Leu  Leu  Gln  Glu  Asp  Thr  Pro  Val  Arg  Lys  Leu  Gln  Ala  Asn  Lys
               760                      765                 770

AAA  AGT  TCA  AGG  ATC  TAGAAGACGA  TTAAGGGAAG  GTCGTTCTCA  GTGAAAATCC              2413
Lys  Ser  Ser  Arg  Ile
               775

AAAAACCAGA  AAAAAATGTT  TATACAACCC  TAAGTCAATA  ACCTGACCTT  AGAAAATTGT                2473

GAGAGCCAAG  TTGACTTCAG  GAACTGAAAC  ATCAGCACAA  AGAAGCAATC  ATCAAATAAT                2533

TCTGAACACA  AATTTAATAT  TTTTTTTTCT  GAATGAGAAA  CATGAGGGAA  ATTGTGGAGT                2593

TAGCCTCCTG  TGGTAAAGGA  ATTGAAGAAA  ATATAACACC  TTACACCCTT  TTTCATCTTG                2653

ACATTAAAAG  TTCTGGCTAA  CTTTGGAATC  CATTAGAGAA  AAATCCTTGT  CACCAGATTC                2713

ATTACAATTC  AAATCGAAGA  GTTGTGAACT  GTTATCCCAT  TGAAAAGACC  GAGCCTTGTA                2773

TGTATGTTAT  GGATACATAA  AATGCACGCA  AGCCATTATC  TCTCCATGGG  AAGCTAAGTT                2833

ATAAAAATAG  GTGCTTGGTG  TACAAAACTT  TTTATGATCA  AAAGGCTTTG  CACATTTCTA                2893

TATGAGTGGG  TTTACTGGTA  AATTATGTTA  TTTTTACAA   CTAATTTTGT  ACTCTCAGAA                2953

TGTTTGTCAT  ATGCTTCTTG  CAATGCATAT  TTTTTAATCT  CAAACGTTTC  AATAAAACCA                3013

TTTTTCAGAT  ATAAAGAGAA  TTACTTCAAA  TTGAGTAATT  CAGAAAAACT  CAAGATTTAA                3073

GTTAAAAAGT  GGTTTGGACT  TGGGAATAGG  ACTTTATACC  TCTTTCTCGT  GCC                       3126
```

( 2 ) INFORMATION FOR SEQ ID NO:4:

( i ) SEQUENCE CHARACTERISTICS:
        ( A ) LENGTH: 777 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Leu  Pro  Ala  Arg  Ile  Leu  Ala  Leu  Ala  Leu  Ala  Leu  Ala  Leu
 1                  5                   10                      15

Gly  Pro  Ala  Val  Thr  Leu  Ala  Asn  Pro  Ala  Arg  Thr  Pro  Tyr  Glu  Leu
               20                  25                      30
```

Val Leu Gln Lys Ser Ser Ala Arg Gly Gly Arg Asp Gln Gly Pro Asn
              35                  40                  45

Val Cys Ala Leu Gln Gln Ile Leu Gly Thr Lys Lys Lys Tyr Phe Ser
        50                  55                  60

Thr Cys Lys Asn Trp Tyr Lys Lys Ser Ile Cys Gly Gln Lys Thr Thr
65                      70                  75                  80

Val Leu Tyr Glu Cys Cys Pro Gly Tyr Met Arg Met Glu Gly Met Lys
                    85                  90                  95

Gly Cys Pro Ala Val Leu Pro Ile Asp His Val Tyr Gly Thr Leu Gly
            100                 105                 110

Ile Val Gly Ala Thr Thr Thr Gln Arg Tyr Ser Asp Ala Ser Lys Leu
            115                 120                 125

Arg Glu Glu Ile Glu Gly Lys Gly Ser Phe Thr Tyr Phe Ala Pro Ser
            130                 135                 140

Asn Glu Ala Trp Asp Asn Leu Asp Ser Asp Ile Arg Arg Gly Leu Glu
145                 150                 155                 160

Ser Asn Val Asn Val Glu Leu Leu Asn Ala Leu His Ser His Met Ile
                165                 170                 175

Asn Lys Arg Met Leu Thr Lys Asp Leu Lys Asn Gly Met Ile Ile Pro
            180                 185                 190

Ser Met Tyr Asn Asn Leu Gly Leu Phe Ile Asn His Tyr Pro Asn Gly
        195                 200                 205

Val Val Thr Val Asn Cys Ala Arg Ile Ile His Gly Asn Gln Ile Ala
        210                 215                 220

Thr Asn Gly Val Val His Val Ile Asp Arg Val Leu Thr Gln Ile Gly
225                 230                 235                 240

Thr Ser Ile Gln Asp Phe Ile Glu Ala Glu Asp Asp Leu Ser Ser Phe
                245                 250                 255

Arg Ala Ala Ala Ile Thr Ser Asp Ile Leu Glu Ala Leu Gly Arg Asp
            260                 265                 270

Gly His Phe Thr Leu Phe Ala Pro Thr Asn Glu Ala Phe Glu Lys Leu
        275                 280                 285

Pro Arg Gly Val Leu Glu Arg Ile Met Gly Asp Lys Val Ala Ser Glu
    290                 295                 300

Ala Leu Met Lys Tyr His Ile Leu Asn Thr Leu Gln Cys Ser Glu Ser
305                 310                 315                 320

Ile Met Gly Gly Ala Val Phe Glu Thr Leu Glu Gly Asn Thr Ile Glu
                325                 330                 335

Ile Gly Cys Asp Gly Asp Ser Ile Thr Val Asn Gly Ile Lys Met Val
            340                 345                 350

Asn Lys Lys Asp Ile Val Thr Asn Asn Gly Val Ile His Leu Ile Asp
        355                 360                 365

Gln Val Leu Ile Pro Asp Ser Ala Lys Gln Val Ile Glu Leu Ala Gly
    370                 375                 380

Lys Gln Gln Thr Thr Phe Thr Asp Leu Val Ala Gln Leu Gly Leu Ala
385                 390                 395                 400

Ser Ala Leu Arg Pro Asp Gly Glu Tyr Thr Leu Leu Ala Pro Val Asn
            405                 410                 415

Asn Ala Phe Ser Asp Asp Thr Leu Ser Met Asp Gln Arg Leu Leu Lys
            420                 425                 430

Leu Ile Leu Gln Asn His Ile Leu Lys Val Lys Val Gly Leu Asn Glu
        435                 440                 445

Leu Tyr Asn Gly Gln Ile Leu Glu Thr Ile Gly Gly Lys Gln Leu Arg

|     |     |     |     | 450 |     |     |     |     | 455 |     |     |     |     | 460 |     |
| --- | --- | --- | --- | --- | --- | --- | --- | --- | --- | --- | --- | --- | --- | --- | --- |
| Val 465 | Phe | Val | Tyr | Arg | Thr 470 | Ala | Val | Cys | Ile | Glu 475 | Asn | Ser | Cys | Met | Glu 480 |
| Lys | Gly | Ser | Lys | Gln 485 | Gly | Arg | Asn | Gly | Ala 490 | Ile | His | Ile | Phe | Arg 495 | Glu |
| Ile | Ile | Lys | Pro 500 | Ala | Glu | Lys | Ser | Leu 505 | His | Glu | Lys | Leu | Lys 510 | Gln | Asp |
| Lys | Arg | Phe 515 | Thr | Thr | Phe | Leu | Ser 520 | Leu | Leu | Glu | Ala | Ala 525 | Asp | Leu | Lys |
| Glu | Leu 530 | Leu | Thr | Gln | Pro | Gly 535 | Asp | Trp | Thr | Leu | Phe 540 | Val | Pro | Thr | Asn |
| Asp 545 | Ala | Phe | Lys | Gly | Met 550 | Thr | Ser | Glu | Glu | Lys 555 | Glu | Ile | Leu | Ile | Arg 560 |
| Asp | Lys | Asn | Ala | Leu 565 | Gln | Asn | Ile | Ile | Leu 570 | Tyr | His | Leu | Thr | Pro 575 | Gly |
| Val | Phe | Ile | Gly 580 | Lys | Gly | Phe | Glu | Pro 585 | Gly | Val | Thr | Asn | Ile 590 | Leu | Lys |
| Thr | Thr | Gln 595 | Gly | Ser | Lys | Ile | Phe 600 | Leu | Lys | Glu | Val | Asn 605 | Asp | Thr | Leu |
| Leu | Val 610 | Asn | Glu | Leu | Lys | Ser 615 | Lys | Glu | Ser | Asp | Ile 620 | Met | Thr | Thr | Asn |
| Gly 625 | Val | Ile | His | Val | Val 630 | Asp | Lys | Leu | Leu | Tyr 635 | Pro | Ala | Asp | Thr | Pro 640 |
| Val | Gly | Asn | Asp | Gln 645 | Leu | Leu | Glu | Ile | Leu 650 | Asn | Lys | Leu | Ile | Lys 655 | Tyr |
| Ile | Gln | Ile | Lys 660 | Phe | Val | Arg | Gly | Ser 665 | Thr | Phe | Lys | Glu | Ile 670 | Pro | Val |
| Thr | Val | Tyr 675 | Arg | Pro | Thr | Leu | Thr 680 | Lys | Val | Lys | Ile | Glu 685 | Gly | Glu | Pro |
| Glu | Phe 690 | Arg | Leu | Ile | Lys | Glu 695 | Gly | Glu | Thr | Ile | Thr 700 | Glu | Val | Ile | His |
| Gly 705 | Glu | Pro | Ile | Ile | Lys 710 | Lys | Tyr | Thr | Lys | Ile 715 | Ile | Asp | Gly | Val | Pro 720 |
| Val | Glu | Ile | Thr | Glu 725 | Lys | Glu | Thr | Arg | Glu 730 | Glu | Arg | Ile | Ile | Thr 735 | Gly |
| Pro | Glu | Ile | Lys 740 | Tyr | Thr | Arg | Ile | Ser 745 | Thr | Gly | Gly | Gly | Glu 750 | Thr | Glu |
| Glu | Thr | Leu 755 | Lys | Lys | Leu | Leu | Gln 760 | Glu | Asp | Thr | Pro | Val 765 | Arg | Lys | Leu |
| Gln | Ala 770 | Asn | Lys | Lys | Ser | Ser 775 | Arg | Ile |     |     |     |     |     |     |     |

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

TGTCCAGATG          10

( 2 ) INFORMATION FOR SEQ ID NO:6:

( i ) SEQUENCE CHARACTERISTICS:
           ( A ) LENGTH: 11 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

T G T C C A G A T G C                                           11

( 2 ) INFORMATION FOR SEQ ID NO:7:

( i ) SEQUENCE CHARACTERISTICS:
           ( A ) LENGTH: 12 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

T G T C C A G A T G A C                                      12

( 2 ) INFORMATION FOR SEQ ID NO:8:

( i ) SEQUENCE CHARACTERISTICS:
           ( A ) LENGTH: 10 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

T G T C C A G A T A                                             10

( 2 ) INFORMATION FOR SEQ ID NO:9:

( i ) SEQUENCE CHARACTERISTICS:
           ( A ) LENGTH: 10 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

T G T C C A G A C G                                             10

( 2 ) INFORMATION FOR SEQ ID NO:10:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

TGTCCAGCCG     10

( 2 ) INFORMATION FOR SEQ ID NO:11:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

TGTCCCGCCG     10

( 2 ) INFORMATION FOR SEQ ID NO:12:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

TGCCCGGCCG     10

( 2 ) INFORMATION FOR SEQ ID NO:13:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

TGATGCACTC     10

( 2 ) INFORMATION FOR SEQ ID NO:14:

( i ) SEQUENCE CHARACTERISTICS:
( A ) LENGTH: 10 base pairs
( B ) TYPE: nucleic acid
( C ) STRANDEDNESS: single (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:14:

TGAGCTACTC 10

(2) INFORMATION FOR SEQ ID NO:15:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:15:

TGACTGACTC 10

(2) INFORMATION FOR SEQ ID NO:16:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:16:

CTGATCCATG 10

(2) INFORMATION FOR SEQ ID NO:17:

(i) SEQUENCE CHARACTERISTICS:
(A) LENGTH: 683 amino acids
(B) TYPE: amino acid
(C) STRANDEDNESS: single
(D) TOPOLOGY: linear (i i) MOLECULE TYPE: protein (i i i) HYPOTHETICAL: NO (i v) ANTI-SENSE: NO (v) FRAGMENT TYPE: internal (x i) SEQUENCE DESCRIPTION: SEQ ID NO:17:

```
Met Ala Leu Phe Val Arg Leu Leu Ala Leu Ala Leu Ala Leu Ala Leu
  1               5                  10                  15

Gly Pro Ala Ala Thr Leu Ala Gly Pro Ala Lys Ser Pro Tyr Gln Leu
             20                  25                  30

Pro Leu Gln His Ser Arg Leu Arg Gly Arg Gln His Gly Pro Asn Val
             35                  40                  45

Cys Ala Val Thr Lys Val Ile Gly Thr Asn Arg Lys Tyr Phe Thr Asn
         50                  55                  60
```

-continued

| | | | | | | | | | | | | | | | |
|---|---|---|---|---|---|---|---|---|---|---|---|---|---|---|---|
| Cys 65 | Lys | Gln | Trp | Tyr | Gln 70 | Arg | Lys | Ile | Cys 75 | Gly | Lys | Ser | Thr | Val | Ile 80 |
| Ser | Tyr | Glu | Cys | Cys 85 | Pro | Gly | Tyr | Glu | Lys 90 | Val | Pro | Gly | Glu | Lys 95 | Gly |
| Cys | Pro | Ala | Ala 100 | Leu | Pro | Leu | Ser | Asn 105 | Leu | Tyr | Glu | Thr | Leu 110 | Gly | Val |
| Val | Gly | Ser | Thr 115 | Thr | Thr | Gln | Leu | Tyr 120 | Thr | Asp | Arg | Thr | Glu 125 | Lys | Leu |
| Arg | Pro | Glu 130 | Met | Glu | Gly | Pro 135 | Gly | Ser | Phe | Thr | Ile 140 | Phe | Ala | Pro | Ser |
| Asn 145 | Glu | Ala | Trp | Ala | Ser 150 | Leu | Pro | Ala | Glu | Val 155 | Leu | Val | Ser | Leu | Val 160 |
| Ser | Asn | Val | Asn | Ile 165 | Glu | Leu | Leu | Asn | Ala 170 | Leu | Arg | Tyr | His | Met 175 | Val |
| Gly | Arg | Arg | Val 180 | Leu | Thr | Asp | Glu | Leu 185 | Lys | His | Gly | Met | Thr 190 | Leu | Thr |
| Ser | Met | Tyr 195 | Gln | Asn | Ser | Asn | Ile 200 | Gln | Ile | His | His | Tyr 205 | Pro | Asn | Gly |
| Ile | Val 210 | Thr | Val | Asn | Cys | Ala 215 | Arg | Leu | Leu | Lys | Ala 220 | Asp | His | His | Ala |
| Thr 225 | Asn | Gly | Val | Val | His 230 | Leu | Ile | Asp | Lys | Val 235 | Ile | Ser | Thr | Ile | Thr 240 |
| Asn | Asn | Ile | Gln | Gln 245 | Ile | Ile | Glu | Ile | Glu 250 | Asp | Thr | Phe | Glu | Thr 255 | Leu |
| Arg | Ala | Ala | Val 260 | Ala | Ala | Ser | Gly | Leu 265 | Asn | Thr | Met | Leu | Glu 270 | Gly | Asn |
| Gly | Gln | Tyr 275 | Thr | Leu | Leu | Ala | Pro 280 | Thr | Asn | Glu | Ala | Phe 285 | Glu | Lys | Ile |
| Pro | Ser | Glu 290 | Thr | Leu | Asn | Arg 295 | Ile | Leu | Gly | Asp | Pro 300 | Glu | Ala | Leu | Arg |
| Asp 305 | Leu | Leu | Asn | Asn | His 310 | Ile | Leu | Lys | Ser | Ala 315 | Met | Cys | Ala | Glu | Ala 320 |
| Ile | Val | Ala | Gly | Leu 325 | Ser | Val | Glu | Thr | Leu 330 | Glu | Gly | Thr | Thr | Leu 335 | Glu |
| Val | Gly | Cys | Ser 340 | Gly | Asp | Met | Leu | Thr 345 | Ile | Asn | Gly | Lys | Ala 350 | Ile | Ile |
| Ser | Asn | Lys 355 | Asp | Ile | Leu | Ala | Thr 360 | Asn | Gly | Val | Ile | His 365 | Tyr | Ile | Asp |
| Glu 370 | Leu | Leu | Ile | Pro | Asp 375 | Ser | Ala | Lys | Thr | Leu 380 | Phe | Glu | Leu | Ala | Ala |
| Glu 385 | Ser | Asp | Val | Ser | Thr 390 | Ala | Ile | Asp | Leu | Phe 395 | Arg | Gln | Ala | Gly | Leu 400 |
| Gly | Asn | His | Leu | Ser 405 | Gly | Ser | Glu | Arg | Leu 410 | Thr | Leu | Leu | Ala | Pro 415 | Leu |
| Asn | Ser | Val | Phe 420 | Lys | Asp | Gly | Thr | Pro 425 | Pro | Ile | Asp | Ala | His 430 | Thr | Arg |
| Asn | Leu | Leu | Arg 435 | Asn | His | Ile | Ile | Lys 440 | Asp | Gln | Leu | Ala 445 | Ser | Lys | Tyr |
| Leu | Tyr | His 450 | Gly | Gln | Thr | Leu | Glu 455 | Thr | Leu | Gly | Gly 460 | Lys | Lys | Leu | Arg |
| Val 465 | Phe | Val | Tyr | Arg | Asn 470 | Ser | Leu | Cys | Ile | Glu 475 | Asn | Ser | Cys | Ile | Ala 480 |
| Ala | His | Asp | Lys | Arg | Gly | Arg | Tyr | Gly | Thr | Leu | Phe | Thr | Met | Asp | Arg |

-continued

```
                              485                      490                      495
     Val  Leu  Thr  Pro  Pro  Met  Gly  Thr  Val  Met  Asp  Val  Leu  Lys  Gly  Asp
                    500                      505                      510

Asn  Arg  Phe  Ser  Met  Leu  Val  Ala  Ala  Ile  Gln  Ser  Ala  Gly  Leu  Thr
                    515                      520                      525

Glu  Thr  Leu  Asn  Arg  Glu  Gly  Val  Tyr  Thr  Val  Phe  Ala  Pro  Thr  Asn
          530                      535                      540

Glu  Ala  Phe  Arg  Ala  Leu  Pro  Pro  Arg  Glu  Ser  Arg  Arg  Leu  Leu  Gly
     545                      550                      555                      560

Asp  Ala  Lys  Glu  Leu  Ala  Asn  Ile  Leu  Lys  Tyr  His  Ile  Gly  Asp  Glu
                    565                      570                      575

Ile  Leu  Val  Ser  Gly  Gly  Ile  Gly  Ala  Leu  Val  Arg  Leu  Lys  Ser  Leu
                    580                      585                      590

Gln  Gly  Asp  Lys  Leu  Glu  Val  Ser  Leu  Lys  Asn  Asn  Val  Val  Ser  Val
                    595                      600                      605

Asn  Lys  Glu  Pro  Val  Ala  Glu  Pro  Asp  Ile  Met  Ala  Thr  Asn  Gly  Val
          610                      615                      620

Val  His  Val  Ile  Thr  Asn  Val  Leu  Gln  Pro  Pro  Ala  Asn  Arg  Pro  Gln
     625                      630                      635                      640

Glu  Arg  Gly  Asp  Glu  Leu  Ala  Asp  Ser  Ala  Leu  Glu  Ile  Phe  Lys  Gln
                              645                      650                      655

Ala  Ser  Ala  Phe  Ser  Arg  Ala  Ser  Gln  Arg  Ser  Val  Arg  Leu  Ala  Val
                    660                      665                      670

Pro  Tyr  Gln  Lys  Leu  Leu  Glu  Arg  Met  Lys  His
                    675                      680
```

( 2 ) INFORMATION FOR SEQ ID NO:18:

( i ) SEQUENCE CHARACTERISTICS:
        ( A ) LENGTH: 206 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

```
     Gly  Glu  Lys  Ser  Leu  Glu  Tyr  Lys  Ile  Arg  Asp  Asp  Pro  Asp  Leu  Ser
     1                    5                        10                       15

Gln  Phe  Tyr  Ser  Trp  Leu  Glu  His  Asn  Glu  Val  Ala  Asn  Ser  Thr  Leu
                    20                       25                       30

Gln  Leu  Arg  Gln  Val  Thr  Val  Phe  Ala  Pro  Thr  Asn  Leu  Ala  Gln  Phe
                    35                       40                       45

Asn  Tyr  Lys  Ala  Arg  Asp  Gly  Asp  Glu  Asn  Ile  Ile  Leu  Tyr  His  Met
                    50                       55                       60

Thr  Asn  Leu  Ala  His  Ser  Leu  Asp  Gln  Leu  Gly  His  Lys  Val  Asn  Ser
     65                       70                       75                       80

Glu  Leu  Asp  Gly  Asn  Pro  Pro  Leu  Trp  Ile  Thr  Arg  Arg  Arg  Asp  Thr
                              85                       90                       95

Ile  Phe  Val  Asn  Asn  Ala  Arg  Val  Leu  Thr  Glu  Arg  Ser  Asn  Tyr  Glu
                         100                      105                      110

Ala  Val  Asn  Arg  His  Gly  Lys  Lys  Gln  Val  Leu  His  Val  Val  Asp  Ser
                         115                      120                      125
```

| | | | | | | | | | | | | | | |
|---|---|---|---|---|---|---|---|---|---|---|---|---|---|---|
|Val|Leu|Glu|Pro|Val|Trp|Ser|Thr|Ser|Gly|Gln|Leu|Tyr|Asn|Pro|Asp|
| |130| | | |135| | | |140| | | | | | |
|Ala|Phe|Gln|Phe|Leu|Asn|Gln|Ser|Glu|Asn|Leu|Asp|Leu|Gly|Leu|His|
|145| | | | |150| | | |155| | | | | |160|
|Arg|Val|Arg|Ser|Phe|Arg|Gln|Arg|Val|Phe|Gln|Asn|Gln|Lys|Gln|Asn|
| | | | |165| | | |170| | | |175| | |
|Asp|Phe|Lys|Leu|Glu|Gly|Lys|His|Thr|Phe|Phe|Ile|Pro|Val|Asp|Glu|
| | | |180| | | |185| | | | |190| | |
|Gly|Phe|Lys|Pro|Leu|Pro|Arg|Pro|Glu|Lys|Ile|Asp|Gln|Lys| | |
| | |195| | | |200| | | | |205| | | | |

(2) INFORMATION FOR SEQ ID NO:19:

(i) SEQUENCE CHARACTERISTICS:
    (A) LENGTH: 200 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:19:

| | | | | | | | | | | | | | | |
|---|---|---|---|---|---|---|---|---|---|---|---|---|---|---|
|Ala|Ala|Ala|Asp|Leu|Ala|Asp|Lys|Leu|Arg|Asp|Asp|Ser|Glu|Leu|Ser|
|1| | | |5| | | |10| | | | |15| | |
|Gln|Phe|Tyr|Ser|Leu|Leu|Glu|Ser|Asn|Gln|Ile|Ala|Asn|Ser|Thr|Leu|
| | | |20| | | | |25| | | | |30| | |
|Ser|Leu|Arg|Ser|Cys|Thr|Ile|Phe|Val|Pro|Thr|Asn|Glu|Ala|Phe|Gln|
| | |35| | | | |40| | | | |45| | | |
|Arg|Tyr|Lys|Ser|Lys|Thr|Ala|His|Val|Leu|Tyr|His|Ile|Thr|Thr|Glu|
| |50| | | | |55| | | | |60| | | | |
|Ala|Tyr|Thr|Gln|Lys|Arg|Leu|Pro|Asn|Thr|Val|Ser|Ser|Asp|Met|Ala|
|65| | | | |70| | | | |75| | | | |80|
|Gly|Asn|Pro|Pro|Leu|Tyr|Ile|Thr|Lys|Asn|Ser|Asn|Gly|Asp|Ile|Phe|
| | | | |85| | | | |90| | | | |95| |
|Val|Gly|Asn|Ala|Arg|Ile|Ile|Pro|Ser|Leu|Ser|Val|Glu|Thr|Asn|Ser|
| | | |100| | | | |105| | | | |110| | |
|Asp|Gly|Lys|Arg|Gln|Ile|Met|His|Ile|Ile|Asp|Glu|Val|Leu|Glu|Pro|
| | |115| | | |120| | | | |125| | | | |
|Leu|Thr|Val|Lys|Ala|Gly|His|Ser|Asp|Thr|Pro|Asn|Asn|Pro|Asn|Ala|
| |130| | | | |135| | | | |140| | | | |
|Leu|Lys|Phe|Leu|Lys|Asn|Ala|Glu|Glu|Phe|Asn|Val|Asp|Asn|Ile|Gly|
|145| | | | |150| | | | |155| | | | |160|
|Val|Arg|Thr|Tyr|Arg|Ser|Gln|Val|Thr|Met|Ala|Lys|Lys|Glu|Ser|Val|
| | | | |165| | | | |170| | | | |175| |
|Tyr|Asp|Ala|Ala|Gly|Gln|His|Thr|Phe|Leu|Val|Pro|Val|Asp|Glu|Gly|
| | | |180| | | | |185| | | | |190| | |
|Phe|Lys|Leu|Ser|Ala|Arg|Ser|Ser| | | | | | | | |
| | |195| | | |200| | | | | | | | | |

MONOCLONAL ANTIBODIES TO TUMOR MARKER TC1 AND METHODS FOR USE OF SAME

CROSS REFERENCE TO RELATED APPLICATIONS

This application is a 371 of PCT/US94/12502, filed Oct. 31, 1994, which is a divisional of prior application Ser. No. 08/146,488, filed Oct. 29, 1993 (now abandoned).

GOVERNMENT RIGHTS

This invention was made in part with U.S. Government support. Therefore, the U.S. Government has certain rights in the invention.

FIELD OF THE INVENTION

This invention relates to proteins that serve as tumor markers for human carcinoma and to methods of isolating differentially expressed genes.

BACKGROUND OF THE INVENTION

Tumor markers for human tumor cells have been largely limited to activated oncogenes and their products, for example, the myc, ras, fos, and erbB2 genes and their encoded oncoproteins. In addition, activated anti-oncogenes, such as RB, p53, and DCC, have been identified in normal cells but do not appear to be present in tumor cells. Oncogene and anti-oncogene products have proven difficult to use as consistent predictors of tumor and normal tissue, respectively, due to the relatively low level of expression of the genes encoding these proteins. Thus, there is a need in the art for a tumor marker which is not only differentially expressed in tumor and normal tissue, but also consistently detectable in human tumor tissue and consistently absent in the corresponding normal tissue.

A common method used to identify genes differentially or uniquely expressed in tumors, in cells responding to growth factors, and in differentiated cell types such as, among others, T cells, adipocytes, neurons, and hepatocytes is the subtractive hybridization technique (S. W. Lee et al., Proc. Natl. Acad. Sci. U.S.A. 80:4699, 1983). A method of differential display of eukaryotic mRNA by means of the polymerase chain reaction (PCR) has recently been developed (P. Liang et al., Science 257:967, 1992). This method utilizes oligo dT linked to two additional bases as the primer for reverse transcription driven by reverse transcriptase. cDNA fragments are then amplified by Taq DNA polymerase-based PCR using an oligo dT primer along with one additional primer. The amplified cDNAs are then resolved by DNA sequencing gels. There is a need in the art for a streamlined and simplified process for isolating cDNAs corresponding to differentially expressed mRNAs.

SUMMARY OF THE INVENTION

The invention is based on the discovery of a novel protein, TC1 (SEQ ID NO:4), which is a tumor marker, particularly for invasive and metastatic tumors, and the gene encoding this protein.

The invention thus encompasses the TC1 protein (SEQ ID NO:4), which is useful as a tumor marker for tumor diagnosis and therapy, particularly for colorectal, breast, and gastrointestinal tumors, and for metastatic tumors emanating from these tumor types. TC1 is also a useful marker in general for tumor cell invasion and metastasis. mRNA encoding TC1 is not expressed in most cultured tumor cells, i.e., in vitro, but is expressed once these cells are grown in vivo. Because later stage and deeply invasive tumors contain higher levels of TC1 protein than other tumor tissues, TC1 appears to be a particularly useful marker for later stage cancers.

TC1 protein may also serve as a target in tumor targeted therapy to prevent tumor cell metastasis and thus invasion of additional organs. For example, a polypeptide fragment of the TC1 protein may be used as an antagonist of TC1 biological activity; e.g., where TC1 biological activity includes invasion and metastasis, the polypeptide fragment may be administered to a patient afflicted with the tumor in order to inhibit the spread of the tumor to other tissues. Alternatively, a truncated portion of TC1 which retains the invasive and metastatic biological activities of the full-length molecule will be useful for screening for antagonists of TC1 activity. Potentially useful polypeptides are described herein.

The invention also encompasses nucleotide probes based on the TC1 nucleotide sequence; e.g., 10, 20, 30, 40, etc. nucleotides in length. Such probes are useful for PCR-based tumor detection and in situ hybridization of tumor tissue sections. In addition, probes whose nucleotide sequences are based on homologies with other genes or proteins having sequences related to TC1, i.e., genes of the TC1 family, two of which are described herein, are useful for detecting additional genes belonging to the TC1 family of genes.

The invention thus also encompasses methods of screening for agents which inhibit expression of the TC1 gene (SEQ ID NO:3) in vitro, comprising exposing a metastatic cell line in which TC1 mRNA is detectable in cultured cells to an agent suspected of inhibiting production of the TC1 mRNA; and determining the level of TC1 mRNA in the exposed cell line, wherein a decrease in the level of TC1 mRNA after exposure of the cell line to the agent is indicative of inhibition of TC1 mRNA production.

Alternatively, the screening method may include in vitro screening of a metastatic cell line in which TC1 protein is detectable in cultured cells to an agent suspected of inhibiting production of the TC1 protein; and determining the level of TC1 protein in the cell line, wherein a decrease in the level of TC1 protein after exposure of the cell line to the agent is indicative of inhibition of TC1 protein production.

The invention also encompasses in vivo methods of screening for agents which inhibit expression of the TC1 gene, comprising
exposing a mammal having tumor cells in which TC1 mRNA or protein is detectable to an agent suspected of inhibiting production of TC1 mRNA or protein; and determining the level of TC1 mRNA or protein in tumor cells of the exposed mammal. A decrease in the level of TC1 mRNA or protein after exposure of the mammal to the agent is indicative of inhibition of TC1 gene expression.

These screening methods are particularly applicable to breast tumor cells, colon tumor cells, or tumor cells of the gastrointestinal tract.

The invention also encompasses a pharmaceutical composition for use in treating a late stage cancer, comprising an effective amount of an inhibitor of TC1, and a method of treating late stage cancer, comprising administering to a mammal afflicted with a late stage cancer a therapeutically effective amount of an inhibitor of TC1. Late stage cancers include those which have become deeply invasive in a tissue or which have metastasized to other tissues.

TC1 is detectable in patient blood, urine, sputum or other body fluid using a monoclonal antibody specific for a TC1 epitope. Thus, the invention also encompasses antibodies specific for TC1, which can easily be prepared in a kit form. Monoclonal antibodies specific for TC1 may be used for tumor imaging to localize tumor position and size. TC1-specific monoclonal antibodies are also useful as screening and diagnostic agents in immunohistochemical staining of tissue sections to distinguish tumor cells from normal cells. Thus, anti-TC1 antibodies are particularly useful where they recognize cells which produce the TC1 protein when such cells are paraffin-embedded and/or formalin-fixed. One example of such an antibody is the monoclonal antibody anti-TC1-1 produced by the hybridoma deposited with the American Type Culture Collection as ATCC Deposit No. HB 11481.

In another aspect, the invention also features a novel method, called palindromic PCR, for identifying and isolating a gene, e.g., a gene which is differentially expressed in different types of tissues. The method is based on the use of short DNA primers and corresponding palindromic nucleotide sequences in the nucleotide sequence to be isolated.

Thus, the invention encompasses a method for producing a double stranded cDNA that includes the steps of contacting an mRNA with a DNA primer under stringent hybridization conditions to form a first hybrid molecule, the primer having a length of from 8 to 12 nucleotides and, preferably, 9 to 11 nucleotides; subjecting the first hybrid molecule to an enzyme having reverse transcriptase activity, to produce a first DNA strand complementary to at least a portion of the mRNA; contacting the first DNA strand with the primer under stringent hybridization conditions to form a second hybrid molecule; and subjecting the second hybrid molecule to an enzyme having DNA polymerase activity, to produce a second DNA strand complementary to the first DNA strand. Preferably, the method also includes the step of amplifying the first and second DNA strands.

In preferred embodiments, a single enzyme provides both the reverse transcriptase activity and the DNA polymerase activity. One example of a suitable such enzyme is rTth DNA polymerase from the thermophilic eubacterium *Thermus thermophilus*.

As used herein, the term "palindromic nucleotide sequences" means that a double stranded DNA molecule contains a specific DNA sequence in both its coding strand and its anti-parallel strand, when those strands are read in the same direction, e.g., 5' to 3'.

The specific sequence of the DNA primer is arbitrary in that it is based upon individual judgment. In some instances, the sequence can be entirely random or partly random for one or more bases. Preferably, the GC content of the primer is between 40% and 60%, most preferably about 50%. In other instances, the arbitrary sequence can be selected to contain a specific ratio of each deoxynucleotide. The arbitrary sequence can also be selected to contain, or not to contain, a recognition site for a specific restriction endonuclease.

The DNA primer can contain a sequence that is known to be a "consensus sequence" of an mRNA of known sequence. As defined herein, a "consensus sequence" is a sequence that has been found in a gene family of proteins having a similar function or similar properties. The use of a primer that includes a consensus sequence may result in the cloning of additional members of a desired gene family.

Palindromic PCR enables genes that are altered in their frequency of expression, as well as those that are constitutively or differentially expressed, to be identified by simple visual inspection and isolated. The method also allows the cloning and sequencing of selected mRNAs, so that the investigator may determine the relative desirability of the gene product prior to screening a comprehensive cDNA library for the full length gene product.

Further objects and advantages of the invention will be apparent in light of the following description and the claims.

BRIEF DESCRIPTION OF THE DRAWINGS

The file of this patent includes at least one drawing executed in color

FIG. 3 shows the nucleotide sequence (described herein as SEQ ID NO:1) and corresponding amino acid sequence (SEQ ID NO:2) of the 636 bp partial TC1 clone.

FIGS. 4A–4D show the nucleotide sequence (SEQ ID NO:3) and corresponding amino acid sequence (SEQ ID NO:4) of the full-length TC1 gene and protein.

FIG. 5 is a sequence comparison of the four internal homologous domains of TC1 (SEQ ID NO:4), each approximately 135 amino acids.

FIGS. 7A and 7B show the amino acid sequence identity between TC1 (SEQ ID NO:4) and Big-h3 (SEQ ID NO:17).

FIG. 9 shows amino acid sequence homology between TC1 (SEQ ID NO:4) and Fasciclin I from Grasshopper (GrF) (SEQ ID NO:18) and Drosophila (DrF) (SEQ ID NO:19).

FIGS. 28A–28D show the corrected nucleotide sequence and corresponding amino acid sequence of the full length TC1 gene and protein.

DESCRIPTION OF THE PREFERRED EMBODIMENTS

TC1 (SEQ ID NO:4) is a novel protein that is found in invasive and metastatic tumor cells. The nucleotide sequence (SEQ ID NO:3) encoding TC1 was found using a novel technique described herein as palindromic PCR, a technique which enables identification and cloning of a gene that is differentially expressed in tissues. Cloning and sequencing of the gene encoding TC1 and characterization of the protein is described below, along with examples of how the protein is detected in invasive and metastatic cancers. Examples describing additional uses of the TC1 protein and its fragments, the nucleotide sequence encoding TC1 and fragments thereof, and antibodies specific for TC1 are also included.

Identification, Cloning and Detection of Expression of the TC1 Gene

Figure 1:
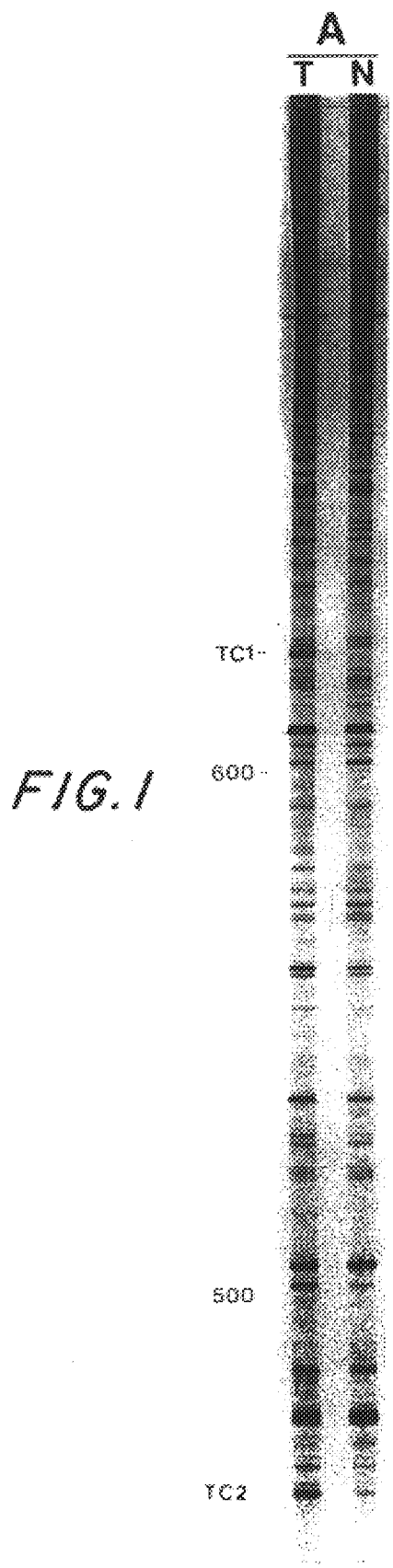
FIG. 1 is a polyacrylamide gel of size-separated cDNAs that were reverse transcribed from paired mRNAs from colon carcinoma (T) and adjacent normal colon tissue (N) and subsequently amplified.
Figure 2A:
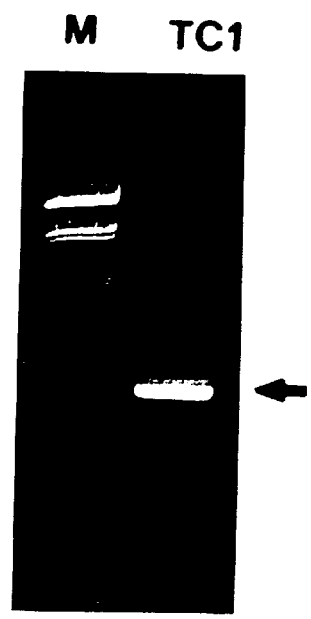
FIG. 2A is a gel in which the TC1 cDNA fragment identified in FIG. 1 was recovered and re-amplified.

The identification, cloning, and differential detection of expression of the TC1 gene (SEQ ID NO:3) was performed as follows. A 636 bp cDNA fragment (SEQ ID NO:1) containing TC1 sequences was identified and isolated by a rapid method termed palindromic PCR, described herein, from human surgical colon carcinoma tissue. Briefly, paired mRNAs were isolated from colon carcinoma tissue and adjacent normal colon tissue from the same patient, then matched mRNAs were reverse transcribed to cDNA and subsequently amplified by the palindromic PCR method described herein, which utilizes one DNA primer. Both reverse transcription and PCR reactions were driven by a single enzyme, rTth DNA polymerase, in a single tube. $^{35}$S or $^{33}$P-labeled PCR cDNA fragments were resolved on a DNA sequencing gel. As shown in FIG. 1, paired mRNAs from colon carcinoma (T) and adjacent normal colon tissue (N) were reverse transcribed to cDNA and subsequently amplified by palindromic PCR. $^{35}$S-labeled PCR cDNA fragments were then resolved on a DNA sequencing gel. A differential cDNA band (TC1) appeared to be present only in the tumor sample. This TC1 cDNA fragment was recovered from the sequencing gel and then reamplified with the same palindromic primer. This 636 bp fragment is identified with a horizontal arrow in FIG. 2A.

Figure 2B:
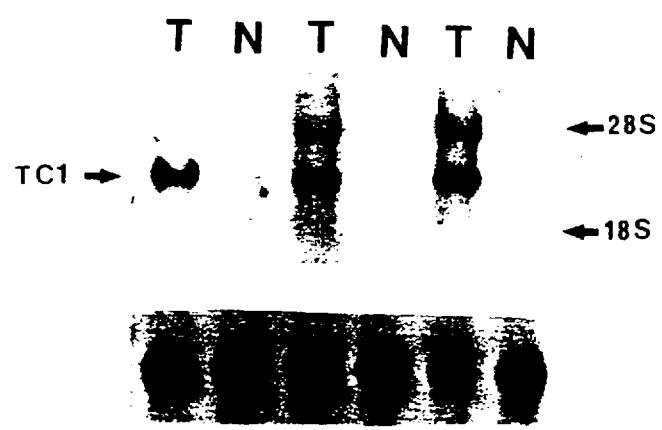
FIG. 2B is a Northern Blot of three pairs of RNA from colon carcinoma (T) and their adjacent normal colon tissue (N) probed with 32P-labeled TC1 cDNA.

TC1 gene expression was examined in colon carcinoma cells and in the corresponding adjacent colon tissue, and the results were as follows. FIG. 2B is a Northern Blot of three pairs of RNA from colon carcinoma (T) and their adjacent normal colon tissue (N) probed with $^{32}$P-labeled TC1 cDNA. TC1 mRNA was over-expressed in all three cases of colon carcinoma, whereas only very weak TC1 message appeared in the adjacent normal tissue. In the bottom panel of the blot, control RNA was blotted with $^{32}$P-labeled cDNA encoding B-actin.

Northern Blot analysis of several pairs of Tumor/Normal total RNA using a $^{32}$P-labeled TC1 cDNA probe revealed that the TC1 mRNA size is about 3.6 Kb. This first TC1 cDNA fragment was cloned into a pBluescript plasmid DNA vector strategies. Nucleotide sequence analysis revealed that this fragment contained 636 bp with nucleotide sequences corresponding to the primer sequence at both 5'-ends of the double-stranded DNA (FIG. 3 and SEQ ID NO: 1). The corresponding predicted amino acid sequence is shown in FIG. 3 and provided in SEQ ID NO: 2. A search of the GenBank database with this cDNA fragment revealed that TC1 is a novel gene.

Figure 4C:
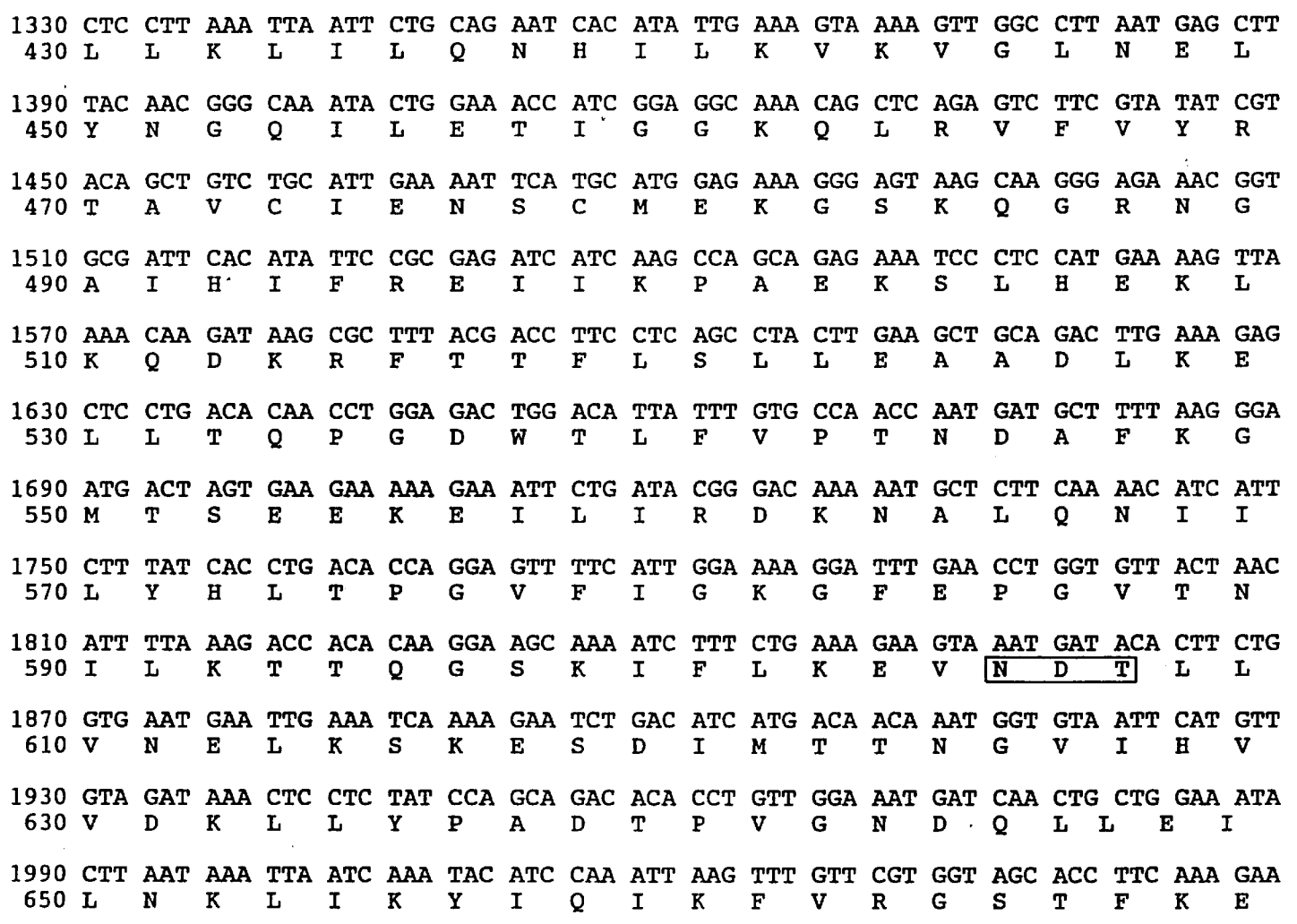
Figure 4D:
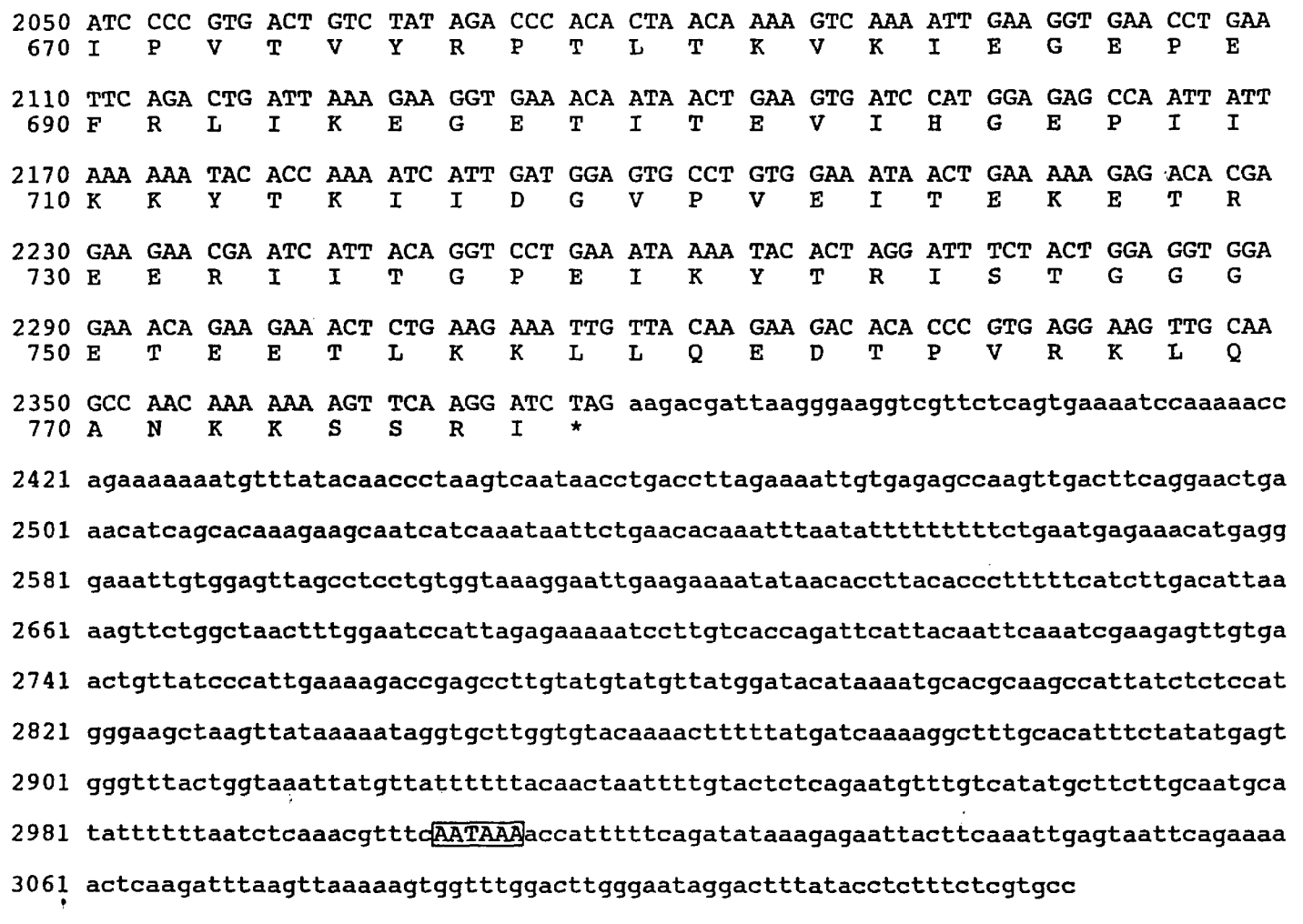

Nucleotide sequence analysis of the 636 bp TC1 cDNA fragment obtained by the described differential display method revealed that it contained a partial open reading frame. Therefore, this 636 bp cDNA fragment was used as probe to screen a cDNA library. Several overlapping clones were obtained and contained a 2997 bp sequence. To obtain the complete open reading frame for TC1, a modified 5'-end RACE technique was used to amplify the TC1 coding regions. The nucleotide and deduced amino acid sequence of full-length TC1 is shown in FIG. 4 and provided in SEQ ID NOS: 3 and 4. The N-terminal signal sequence is underlined; one predicted N-linked glycosylation site (NDT) is boxed and a polyadenylation signal (SEQ ID NO:3, nucleotide residues 3004–3009) is indicated. The cDNA contains 3126 bp with a potential polyadenylation sequences at the 3'-end, beginning at residue 3004 (SEQ ID NO:3, nucleotide residues 3004–3009). The open reading frame (ORF) encodes a 777-amino acid protein with a calculated molecular weight of 86 kD. The TC1 protein contains an amino-terminal signal peptide or secretory leader signal (SEQ ID NO:4, amino acid residues 2–16), and one predicted site of N-linked glycosylation at amino acid residue 605 (NDT). One Cemokine B family motif (C-C) was found at amino acid residue 85 (C-C) of TC1.

Figure 5:
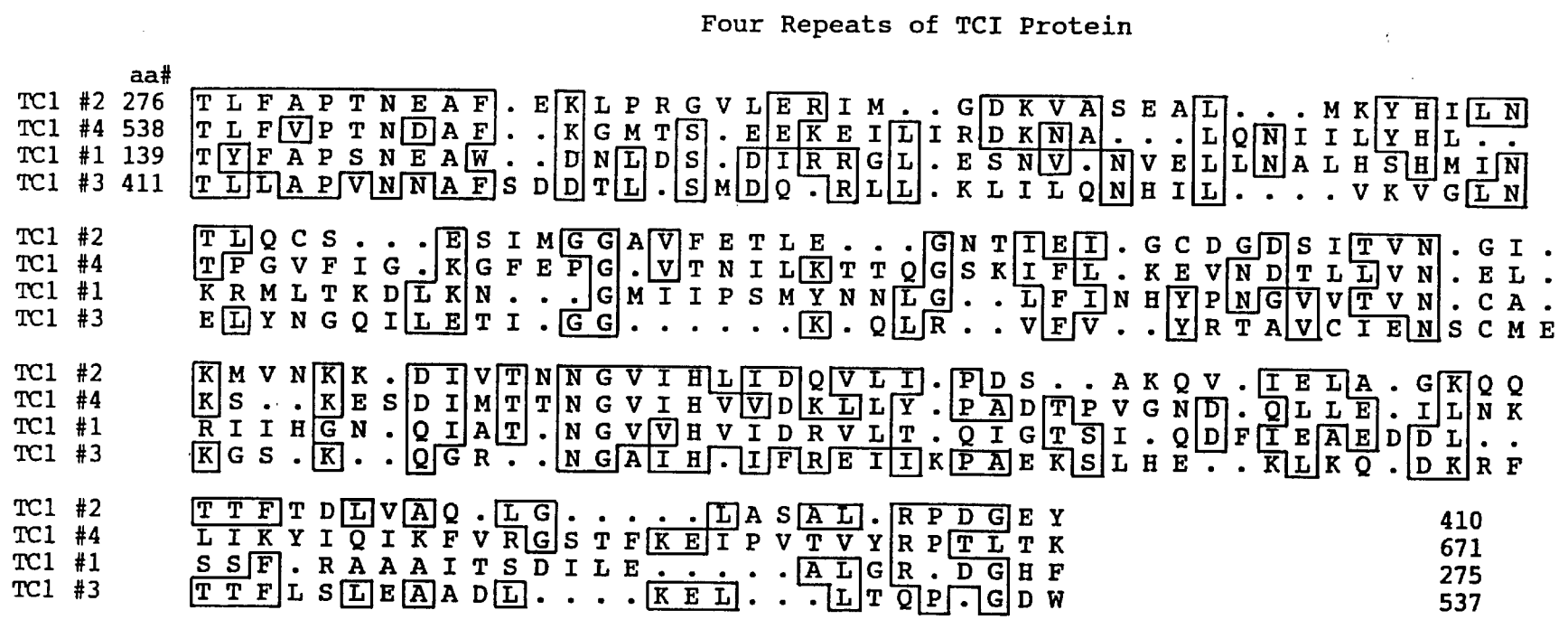
Figure 6:
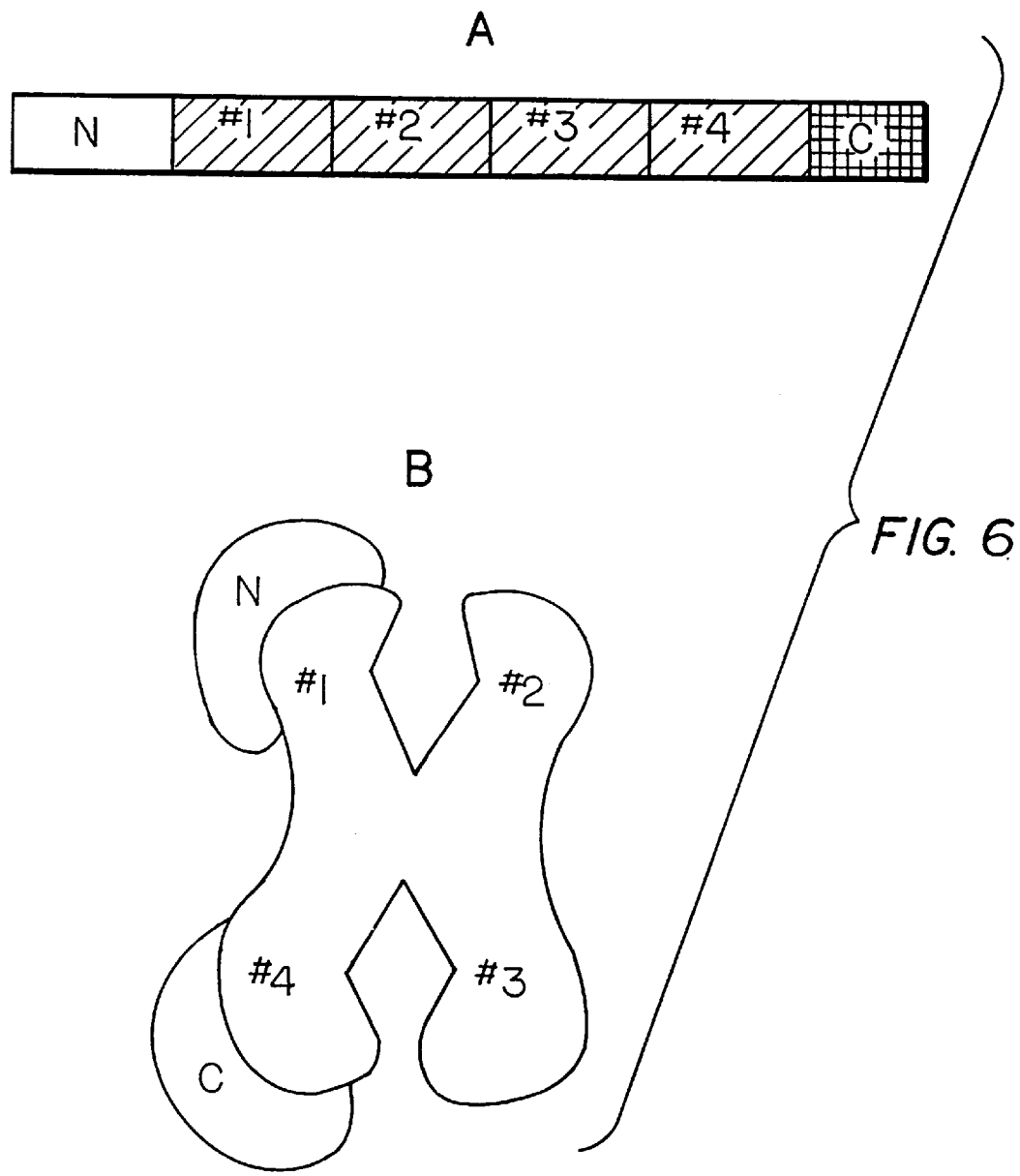
FIG. 6A is a schematic representation of the four repeats of TC1.
FIG. 6B is a proposed schematic arrangement of the four repeated domains and the N- and C-terminal domains.

Analysis of the deduced amino acid sequence (SEQ ID NO:4) revealed that TC1 contained four internal homologous domains of approximately 135 amino acids. A comparison of these repeats is shown in FIG. 5. Each boxed amino acid is identical with at least one other residue at that same position. The interdomain homologies range from 32% (between domains 2 and 4) to 18% (between domains 1 and 3). Some amino acids sequences are highly conserved among all four repeats. Each repeat starts with the most divergent sequence. The four repeats occur between residues 139–537 and are uninterrupted by non-homologous domains. A schematic representation of the four repeats of TC1 is shown in FIG. 6A. The four homologous repeats suggest a tetrameric structure (Mclachlan 1980; Zinn et al, 1988) with two binding sites, one at each intrachain dimer. The four repeats of TC1 may serve as ligand binding sites, with the N-terminal or C-terminal domains serving as the functional domain. One possible arrangement of the four repeated domains and the N- and C-terminal domains is shown schematically in FIG. 6B.

The nucleotide and corresponding amino acid sequence of the TC1 gene and protein with a corrected leader signal sequence are given in FIGS. 28A–28D.

Palindromic PCR

Described below is a novel technique used to identify the TC1 mRNA and prepare TC1 cDNA. Although the sequence of bases in a coding and antisense strand of a cDNA molecule are, in a sense, "mirror images" of one another, we have found that with surprising frequency a short sequence of bases, e.g. 9 or 10, in one strand will be found to have an exact copy in its anti-parallel strand. We call these sequences "palindromic" sequences. This phenomenon has been used to develop a method of cDNA isolation and amplification.

Figure 10:
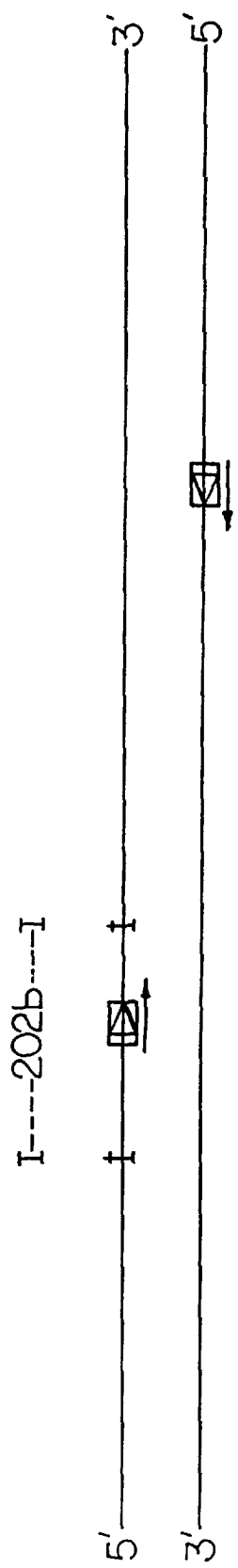
FIG. 10 is a Schematic representation showing that, on average, in every 202 bases of sequence in one strand of cDNA, there is one 9-base sequence exactly palindromic to that in a region of its antiparallel strand.
Figure 11:
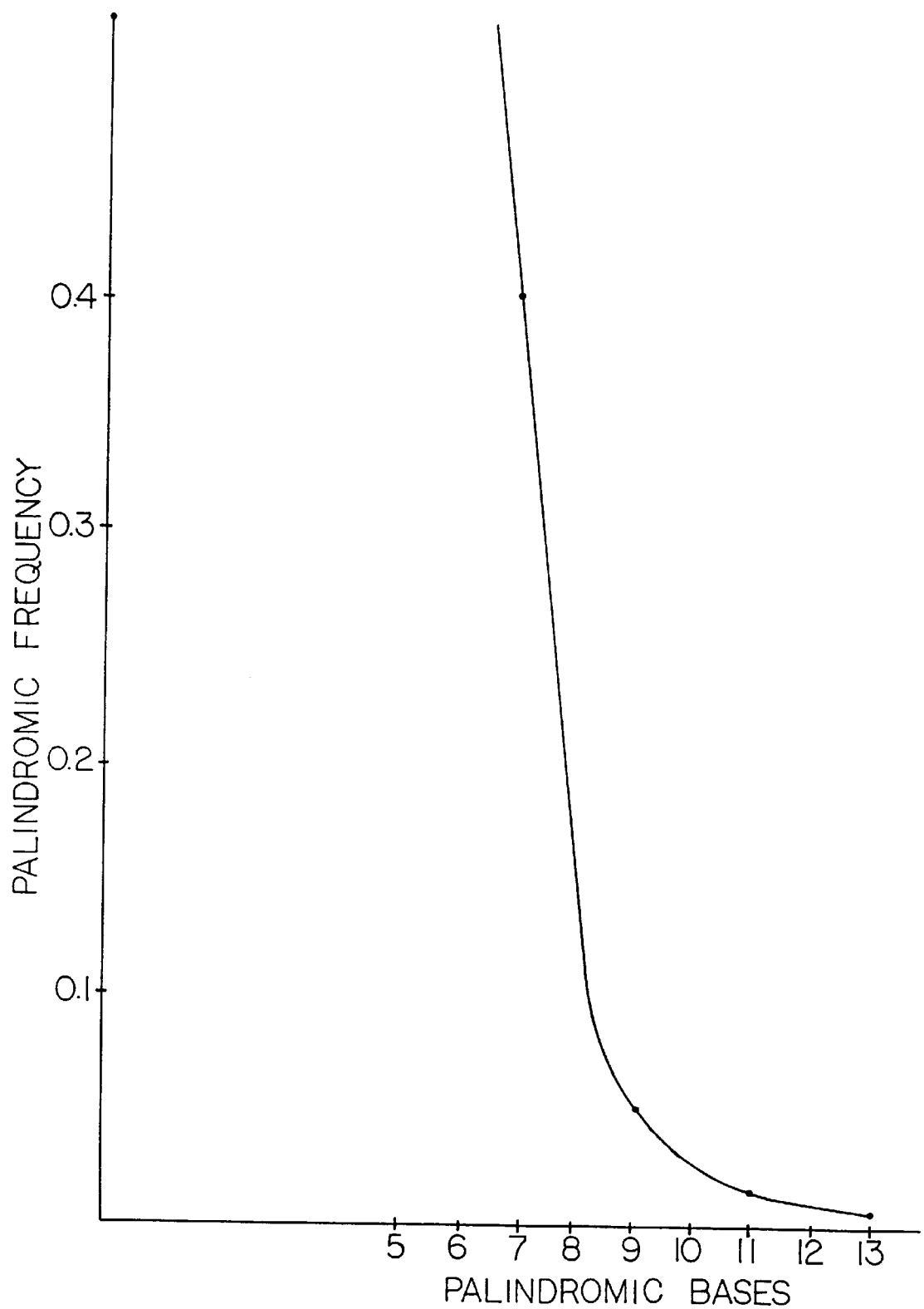
FIG. 11 shows the relationship between the palindromic frequency and the number of bases in a putative DNA primer, as determined by cDNA Matrix analysis.

In order to determine the frequency of occurrence or "palindromic frequency" of these anti-parallel repeats, a computer program called DNA Matrix (DNA Strider 1.2) was used to analyze double stranded cDNAs which were randomly selected from the GenBank database. DNA matrix analysis revealed the palindromic frequency of double strand cDNA to be surprisingly high and led to our development of a relationship between the number of bases in the chosen sequence, the "palindromic bases," and the palindromic frequency. Single strand cDNA (the mRNA strand) and its anti-parallel strand were compared, each from the 5' to 3' end by the DNA Matrix program. For example, as illustrated in FIG. 10, on the average, in every 202 bases of sequence in one strand of cDNA, there is one 9-base sequence that is exactly duplicated to that in another region of its antiparallel strand. The palindromic frequency found in native cDNA is much higher than that which would be calculated from random composition, suggesting that the nucleotide composition of double-stranded cDNA follows certain palindromic rules. As shown in FIG. 11, the palindromic frequency dramatically decreases when the number of bases in the searched segment increases. The key numbers of bases which lead to dramatic change of palindromic frequency are 9, 10 and 11 bases. This, then, is the theoretical basis for designing a primer for use in the DNA isolation and amplification method of the invention, palindromic PCR.

Table 1 presents the statistical data showing the palindromic frequency related to the number of bases in the searched segment.

TABLE 1

Palindromic Frequency Related to
No. of Bases in Searched Segment as
Revealed by cDNA Matrix
Analysis

| No. Bases in Searched Segment (X Bases) | Average Length to Find One X-Base Palindromic Sequence | Palindromic Frequency |
| --- | --- | --- |
| 7 bases | 18 bases | 0.4 |
| 9 bases | 202 bases | 0.048 |
| 11 bases | 872 bases | 0.015 |
| 13 bases | >1996 bases | <0.007 |

Figure 12:
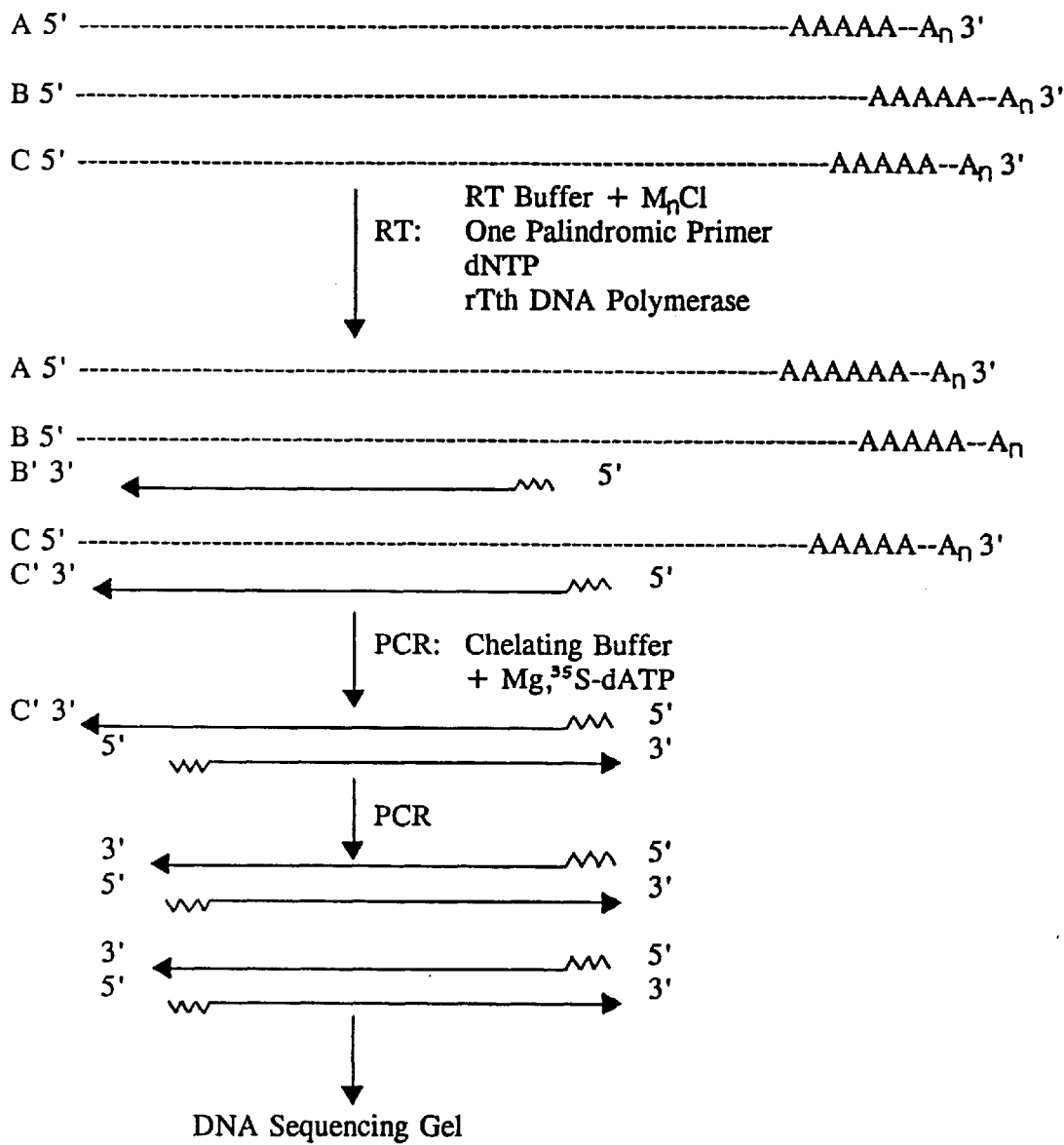
FIG. 12 is a schematic representation of the method of the invention, palindromic PCR, driven by the enzyme rTth DNA polymerase with one DNA primer in one reaction tube; the dotted line indicates mRNA and the solid line indicates cDNA; the short jagged line represents the single DNA primer.
Figure 13A:
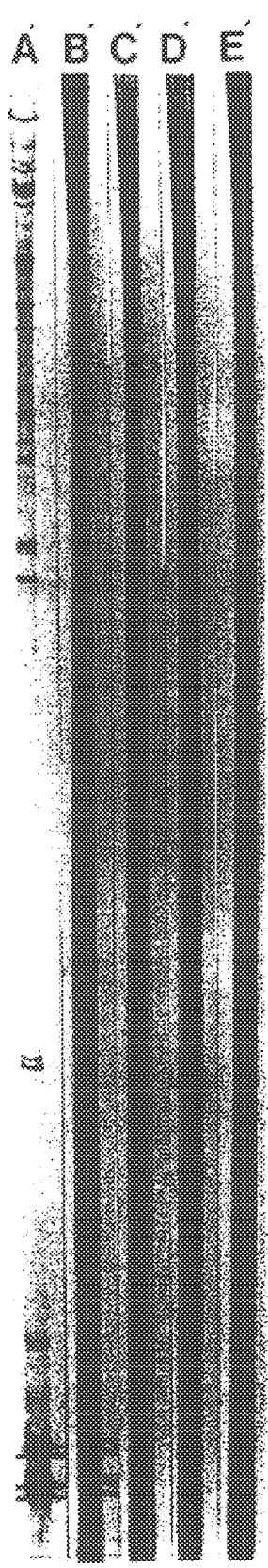
FIG. 13A shows the effect of the length of the DNA primer on the cDNA amplification patterns; the length and nucleotide sequence of each primer are: A, 8-mer (5'-TGTCGAGA); B', 9-mer (5'-TGTCCAGAC); C', 10-mer (5'-TGTCCAGATG) (SEQ ID NO:5); D', 11-mer (5'-TGTCCAGATGC) (SEQ ID NO:6); E', 12-mer (5'-TGTCCAGATGAC) (SEQ ID NO:7).
Figure 13B:
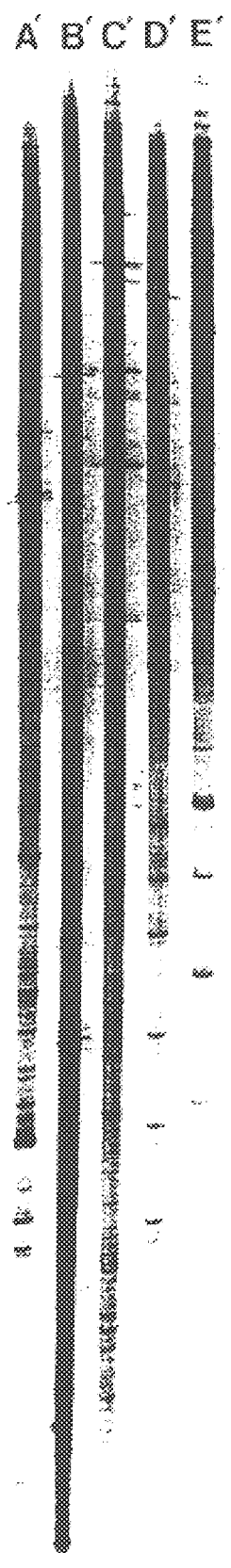
FIG. 13B shows the effect of the GC content of the DNA primer on the cDNA amplification patterns; the GC content and nucleotide sequence of each primer (10-mer) are: A', 40% (5'-TGTCCAGATA) (SEQ ID NO:8); B', 50% (5'-TGTCCAGATG) (SEQ ID NO:5); C', 60% (5'-TGTCCAGACG) (SEQ ID NO:9); D', 70% (5'-TGTCCAGCCG) (SEQ ID NO:10); E', 80% (5'-TGTCCCGCCG) (SEQ ID NO:11); F', 90% (5'-TGCCCGGCCG) (SEQ ID NO:12).
Figure 13C:
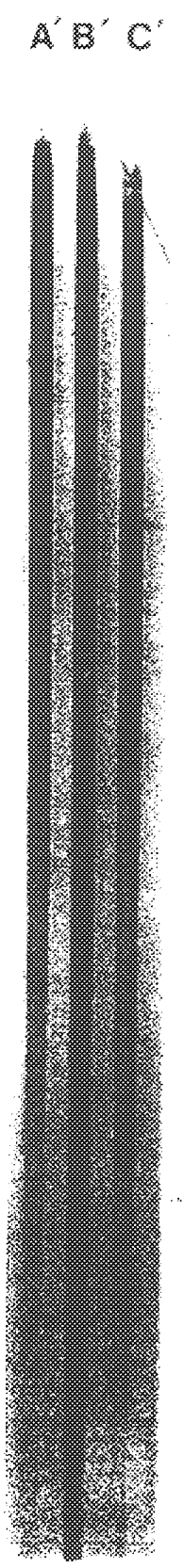
FIG. 13C shows the effect of the sequence specificity of the DNA primer on the cDNA amplification patterns; 10-mer primers with the same GC content but different sequences are: A', 5'-TGATGCACTC (SEQ ID NO:13); B', 5'-TGAGCTACTC (SEQ ID NO:14); C', 5'-TGACTGACTC (SEQ ID NO:15).
Figure 13D:
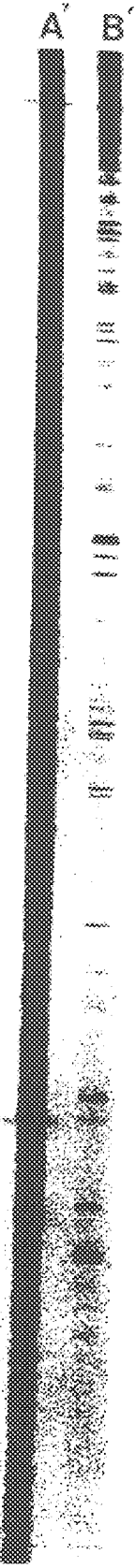
FIG. 13D shows palindromic PCR performed by rTth DNA polymerase (A) with reverse transcription cycles (RT cycles) and (B) without RT cycles.

The principle of the method of palindromic PCR is shown in schematic representation in FIG. 12. The general strategy is to use a single primer and one enzyme combining both reverse transcriptase and DNA polymerase activities, e.g., rTth DNA polymerase (from the thermophilic eubacterium *Thermus thermophilus*), to perform both reverse transcription and polymerase chain reaction in one reaction tube. rTth DNA polymerase possesses a very efficient reverse transcriptase activity in the presence of $MnCl_2$ and a thermostable DNA polymerase activity in the presence of $MgCl_2$. The rTth DNA polymerase has been observed to be greater than 100-fold more efficient in coupled reverse transcription and PCR than the analogous DNA polymerase, Taq (T. W. Myers et al., Biochemistry 30:7661, 1991). In this reaction, an appropriate primer would allow anchored annealing to some regions of certain mRNA species that contain sequence complementary to the palindromic primer. This subpopulation of mRNAs is likely to be reverse transcribed by rTth DNA polymerase. A "Palindromic" primer apparently has a greater probability of anchoring to the coding regions of mRNA than oligodT primer. Once mRNAs are reverse transcribed to form a first strand cDNA species, the same primer can anneal to some regions of the first strand cDNA and function as the "Downstream primer" in a PCR reaction. The same primer can also function as the "Upstream primer." When the primer anchors to first strand cDNAs, the annealing position to various cDNA molecules should, in principle, be at different distances in different molecules from the first annealing position. Therefore, the amplified cDNA fragments from various mRNAs will be of different sizes. Once these PCR-generated cDNA fragments are labeled with [35]S-dATP or [33]P-dATP, they can be resolved as a ladder by DNA sequencing gels. A display of cDNAs originating from various mRNAs can then be visualized after autoradiography.

The selection of the specific palindromic primer depends on three important factors: the length, the GC content, and the sequence specificity. DNA Matrix analysis has indicated that the ideal length of a primer for an appropriate palindromic frequency is from 9 to 11 bases. Therefore, a set of primers from 8 base to 12 base in length with 50% GC content was chosen for study. Our results showed that 9, 10, and 11 base primers gave an appropriate number of cDNA fragments readily resolvable by DNA sequencing gels (FIG. 13). To identify the GC content of the primer most suitable for this method, a set of 10-mer primers with GC content ranging from 40% to 90% was tested. The results suggested that a GC content from 40% to 80% is acceptable (FIG. 13). However, primers with 40% to 60% GC content appear to yield better results. To examine the effect of the specific sequence of the primer, 10-mer primers of different sequences each having 50% GC content was tested. As predicted, different primers gave rise to different cDNA patterns (FIG. 13). As little a difference as three bases led to totally different cDNA profiles.

cDNA patterns generated by palindromic PCR are highly stable. When the same conditions were used but the experiments repeated at different times, the patterns of the amplified cDNA fragments were highly reproduced, indicating the reliability of this method.

In order to be sure of detecting mRNAs with a low copy number, it was necessary to determine the sensitivity of this method. It has been reported that the amplification driven by rTth DNA polymerase is at least 100-fold greater than that by Taq polymerase. rTth DNA polymerase allows the detection of IL-1a mRNA, which has a very low copy number, in 80 pg of total cellular RNA (T. W. Myers et al., Biochemistry 30:7661, 1991). Thus, the higher efficiency of rTth DNA polymerase ensures that the palindromic PCR method of the invention provides high sensitivity. In addition, because rTth polymerase is thermostable, it can also be used to perform several RT cycles (reverse transcription cycles), which means several copies of first strand cDNA can be obtained from a single copy of mRNA. The sensitivity of the method is increased by performing multiple RT cycles using rTth polymerase (FIG. 13).

Figure 14A:
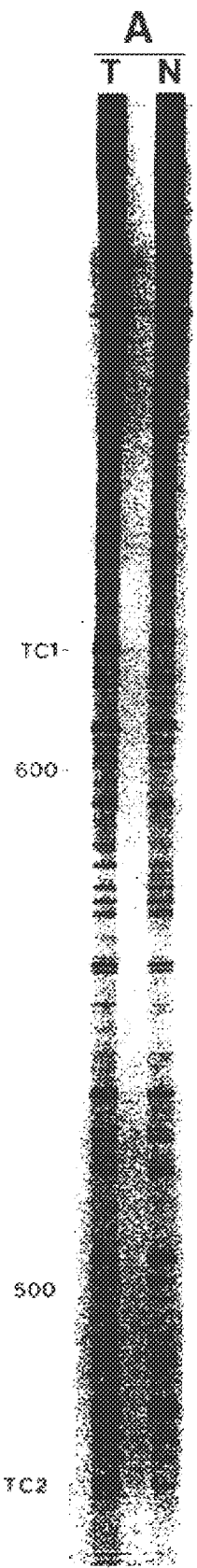
FIGS. 14A and 14B show the identification of differentially expressed genes in human colon carcinoma.
Figure 14B:
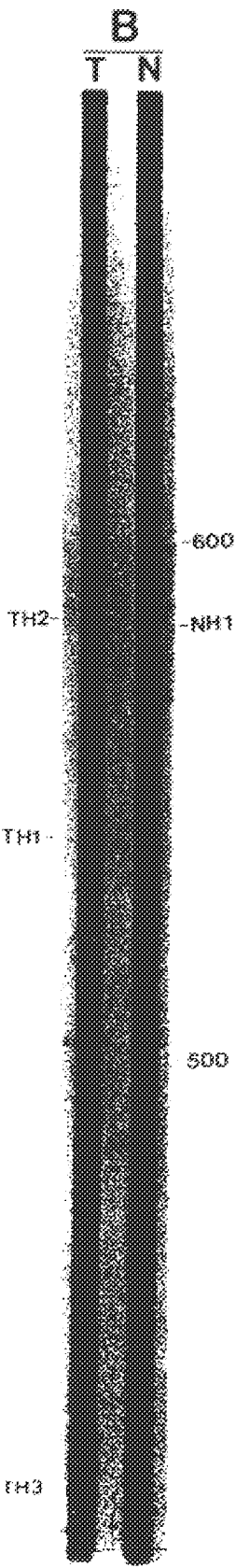

The method of the invention was tested in a search for differences in mRNA expression between human colon carcinoma and the adjacent normal epithelium from a surgical specimen. Paired mRNA preparations were reverse transcribed with a palindromic primer 5'-CTGATCCATG (designated as PP-1 primer) (SEQ ID NO:16) in the presence of $MnCl_2$ followed by PCR with the same primer in the presence of $MgCl_2$ using rTth DNA polymerase. The reaction products were then analyzed by DNA sequencing gels. About 70–110 amplified cDNA fragments ranging from 100–700 bases from both preparations were detected (FIG. 14). Whereas overall cDNA patterns between tumor and normal tissue are similar, significant differences were detected by this method. Most cDNA bands showed the same intensity between tumor and normal preparations, but two cDNA bands designated as TC1 and TC2 appeared with increased intensities in tumor tissue (FIG. 14). A sample reaction protocol is described below.

To 1.1 μl of double distilled (dd) $H_2O$ is added 0.5 μl of 10× rTth DNA polymerase reverse transcriptase (RT) buffer (100 mM Tris-Hcl, pH 8.3, 900 mM KCl), 0.5 μl of 10 mM $MnCl_2$, 0.4 μl of 2.50 mM dNTP, 1.0 μl (0.50 μg) of one palindromic primer (9–11 mer), and 1.0 μl (100 ng) of mRNA to form Mix A in a total vol. of 4.5 μl. Mix A is heated in a 0.5 ml PCR tube at 65° C. for 6 min and then at 37° C. for 8 min. Next, 0.5 μl (1.25 unit) of rTth DNA polymerase is added, the reaction mixture is mixed well, spun briefly, incubated at 70° C. for 12 min and then placed on ice. Mix B which consisting of 12.5 μl of dd $H_2O$, 2.0 μl of 10× chelating buffer (50% glycerol (v/v), 100 mM Tris-HCl, pH 8.3, 1M KCl, 0.5% Tween 20), 2.0 μl of 25 mM $MgCl_2$ solution, 2.50 mM dNTP and 2.0 μl of [35]S-dATP (or [33]P-dATP) is dispensed in the amount of 20 μl into each 5.0 μl RT reaction mixture. The samples are mixed and spun briefly and then overlaid with 25 μl of mineral oil. The polymerase chain reaction is then started: 94° C. for 40 sec., 40° C. for 2 min., 72° C. for 35 sec. (for 40 cycles, hold at 72° C. for 4 min.), and then 4° C.

For cDNA analysis, 7 μl of a PCR sample is mixed with 4 μl of sequencing loading buffer, samples are incubated at 80° C. for 3 min., and then placed on ice. 4.5 μl of the sample is loaded on a 6%–8% agarose DNA sequencing gel.

Figure 15:
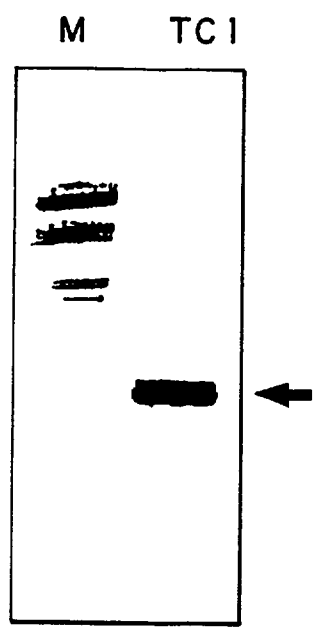
FIG. 15 shows reamplification of the TC1 cDNA fragment isolated from colon carcinoma; the PCR product was analyzed on a 1.0% agarose gel; a 0.63 Kb cDNA fragment (arrow) was detected.

A gel slice containing a desirable cDNA band (such as TC1) was soaked in 200 μl of dd$H_2O$ for 20 min and then separated from 3M paper with a clean forcep or a plastic pipette tip. The gel was removed and pounded with an autoclaved plastic pipette tip. Elution buffer (20 μl) was added and the mixture was vortexed and left at room temperature for 4 hrs or overnight. After centrifugation, cDNA fragments in 10 μl eluent were reamplified by rTth DNA polymerase with the same palindromic primer, as described. After one 40-cycle PCR, the reamplified cDNA could be detected by agrose gels stained with ethidium bromide. The amount of cDNA generated was sufficient for cloning and preparing a probe for Northern Blot analysis. FIG. 15 shows the gel obtained when the TC1 cDNA band was subjected to elution and reamplification. Total PCR product of the TC1 fragment was 2.5 μg.

Figures 16A, 16B:
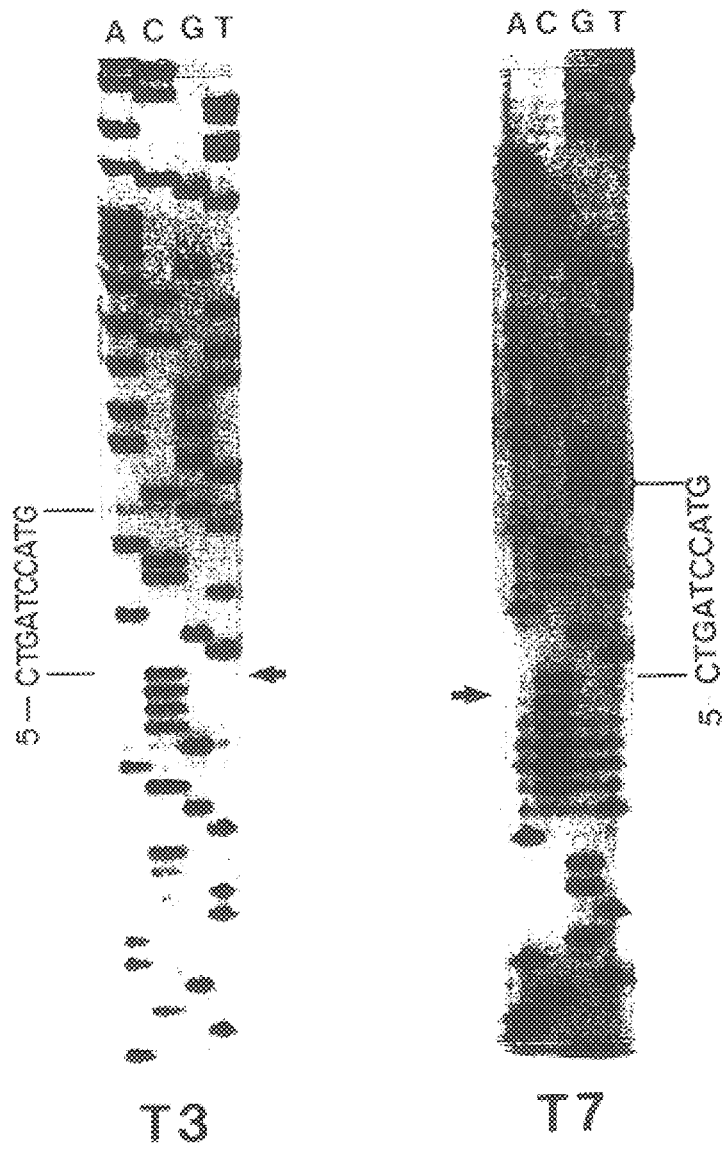
FIGS. 16A and 16B show is an autoradiogram of DNA sequencing gels showing the presence of PP1 primer sequence (5'-CTGATCCATG) (SEQ ID NO:16) at the 5'-end of both strands of the TC1 cDNA fragment; cloning sites are indicated by arrows, sequences below arrows are pBS (KS) vector sequences reading from T3 primer and T7 primer.

The reamplified TC1 cDNA fragment was treated with T4 DNA polymerase and cloned into pBluescript plasmid DNA vector at SmaI site by blunt end ligation. The nucleotide sequence of the TC1 fragment (SEQ ID NO:1) showed that a sequence identical to the PP1 primer (SEQ ID NO:16) is indeed present at the 5'-end of both strands of the TC1 fragment (FIG. 16). This result confirms that the 5'-ends of both complementary chains of the TC1 cDNA fragment used the same palindromic primer during palindromic PCR as discussed above. It also implies that the same palindromic primer sequence is present at the 5'-ends of both strands for every PCR product in the same reaction. These results establish that a single 9–11 base palindromic primer can effectively prime reverse transcription and then serve as both a "Downstream primer" and an "Upstream primer" in palindromic PCR amplification.

The method of the invention differs from other methods in a number of ways. In palindromic PCR, only a single primer (9–11 bases) is used and is sufficient to prime reverse transcription as well as to support subsequent PCR for a display of nearly 100 cDNA species. Because the pattern of amplified cDNAs depends on the sequence of the single palindromic primer, the species of mRNAs that are subjected to amplification can readily be controlled by a proper sequence of the palindromic primer. If a group or family of genes shares certain sequences, a primer can be chosen from such a sequence, and a specific display of this set of mRNAs can readily be performed. Likewise, computer analysis of the Genebank database may reveal additional sequences useful as a primer shared by a set of related genes. The use of such a primer by the method of the invention would allow the display for the expression of a given set of genes. Palindromic PCR provides an easy, sensitive and economical way to identify and isolate differentially expressed genes related to tumor and other disease.

Differential expression of TC1 DNA in normal tissue and tumor cells

Northern Blot analysis, as described above, confirmed the differential expression of TC1 mRNA in colon carcinoma tissue, and the absence of TC1 mRNA in the corresponding normal tissue. Evaluation of the expression of TC1 mRNA in additional cases of colon carcinoma at different stages was also undertaken. Surgical specimens of 24 cases of human primary colon carcinoma and 6 cases of liver metastases were examined by Northern hybridization of total RNA with $^{32}$P-labeled TC1 probe.

Figure 17A:
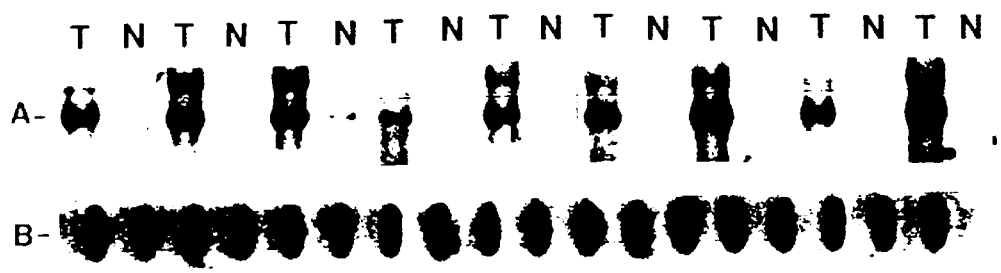
FIGS. 17A–17C show is a Northern Blot of 24 pairs of colon carcinoma (T) and their adjacent normal tissue (N) probed with 32P-labeled TC1 cDNA.
Figure 17B:
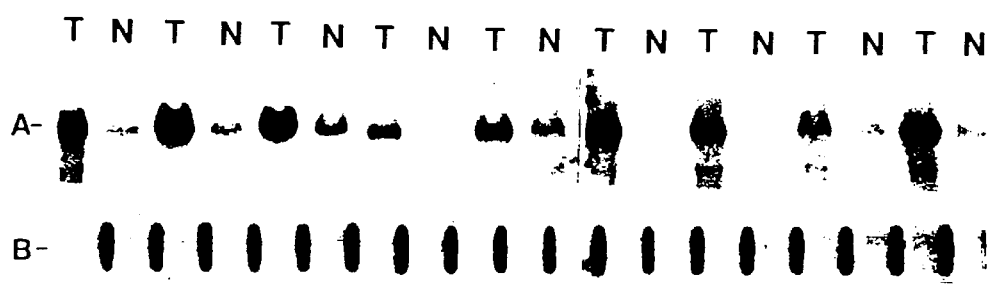
Figure 17C:

A Northern Blot of 24 pairs of colon carcinoma (T) and their adjacent normal tissue (N) probed with $^{32}$P-labeled TC1 cDNA is shown in FIG. 17. It is evident from the results that the level of TC1 mRNA in tumor tissue is much greater than the level in adjacent normal tissue in all 24 cases. The TC1 mRNA levels vary in different cases of carcinoma. Panels I and II show A: TC1 mRNA and B: Control; Panel III shows TC1 mRNA and control (Actin) mRNA.

Figure 18:
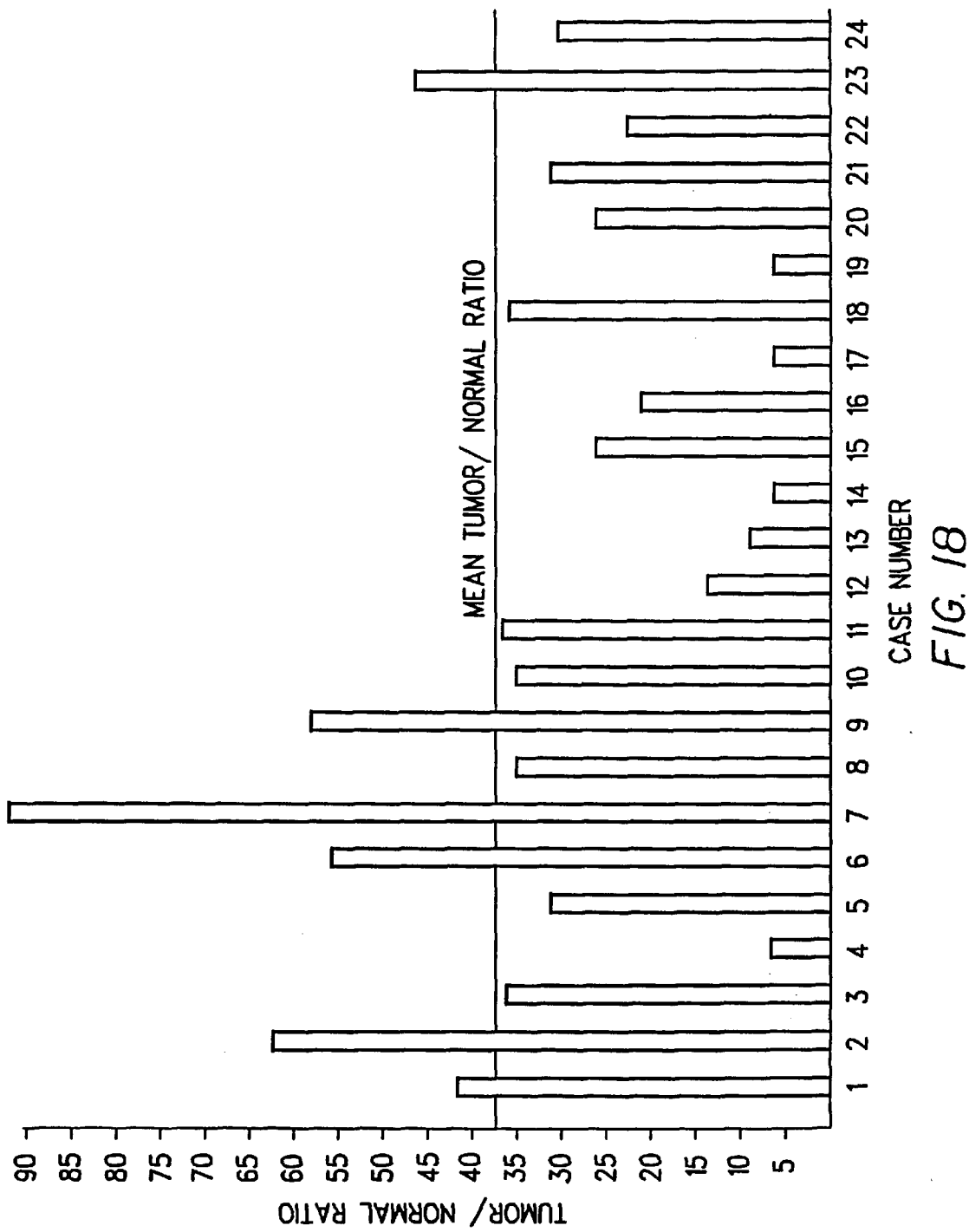
FIG. 18 shows the Tumor/Normal RNA Ratio from Northern Blot results of FIG. 17.

FIG. 18 shows the Tumor/Normal RNA Ratio from Northern Blot results of FIG. 17. The horizontal line indicates the mean Tumor/Normal ratio. TC1 mRNA was abundantly expressed in all 24 cases of primary colon carcinoma and 6 cases of liver metastases, whereas only a small amount of TC1 mRNA was detected in a few cases of paired adjacent normal tissue. The mRNA level of TC1 was much greater in primary colon carcinoma than in paired adjacent normal colonic epithelium in all 24 cases. The Tumor/Normal ratio varied from 5.6 to 92, and the mean Tumor/Normal ratio being 32. The Tumor/Normal ratio, when plotted against the Duke's stage of disease, gave evidence for increasing TC1 expression with increasing stage of colon carcinoma.

Figure 19:
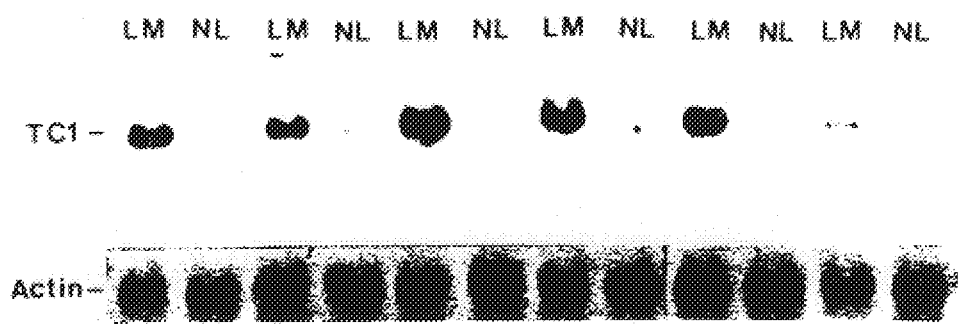
FIG. 19 is a Northern Blot of RNA from carcinoma cells which result from metastasis from colon carcinoma to liver (LM) and their adjacent normal liver (NL) probed with $^{32}$P-labeled TC1 cDNA.

In all six cases of paired colon carcinoma metastatic to liver, the TC1 mRNA level was much higher in metastatic tumor than in adjacent normal liver tissue. FIG. 19 shows a Northern Blot of RNA from metastatic colon carcinoma to liver (LM) and their adjacent normal liver (NL) probed with $^{32}$P-labeled TC1 cDNA. TC1 mRNA was expressed only in metastatic tumor in 5 of 6 samples. Only one sample of normal liver tissue expressed a very weak TC1 message. The Tumor/Normal ratio is greater than 64. These results suggested that differential expression of TC1 may be associated with human colorectal cancer progression and biological aggressiveness of the disease.

In vivo and in vitro expression of TC1 mRNA

The expression of TC1 mRNA in cultured cancer cells and in vivo tumor cells was analyzed and is described below. TC1 was overexpressed in tumor tissue in vivo. The expression of TC1 mRNA in cultured cancer cell lines in vitro was examined by Northern Blot analysis. RNAs isolated from twelve colon cancer cell lines (HT29, Clone A, MIP101, CX-1, Morser, CCL227, CCL228, etc.) derived from different stage of human colon carcinoma, two melanoma cell lines (LOX, A2058), one breast cancer cell line (MCF-7), two cervical cancer cell lines (Hela, A431), three bladder cancer cell lines (EJ, T24, MB49), one pancreas cancer cell line (CRL1420), two hepatoma cell lines (HepG2, HepG3) and four normal cell lines (FS-2, MRC-5, 498A, CV-1) were screened by Northern Blot analysis. However, the TC1 transcript could not be detected in all of these cell lines. This result suggested that TC1 expression was dramatically decreased or indeed turned off in cultured cancer cells. However, after cultured cancer cells were injected into nude mice to grow tumor in vivo, TC1 mRNA expression turned on again and its mRNA level could be detected by Northern Blot analysis.

Figure 20:
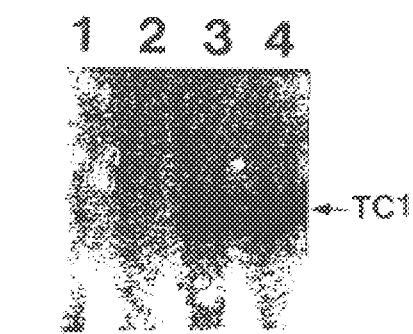
FIG. 20 shows a Northern Blot of RNA from breast cancer cell line MCF-7 (1) and colon cancer cell line CX-1 (2) cultured in vitro, and MCF-7 tumor (3) and CX-1 tumor (4) grown in vivo in nude mice.

FIG. 20 shows a Northern Blot of RNA from breast cancer cell line MCF-7 (1) and colon cancer cell line CX-1 (2) cultured in vitro, and MCF-7 tumor (3) and CX-1 tumor (4) grown in vivo in nude mice. TC1 mRNA in colon cancer cell line CX-1 and breast cancer cell line MCF-7 cultured in vitro could not be detected by Northern Blot analysis. After cultured CX-1 and HT29 cells were injected into nude mice to form tumors in vivo, TC1 mRNA was detectable by Northern Blot analysis, the TC1 mRNA levels being dramatically increased in vivo. This result suggests that TC1 gene expression was turned on or dramatically increased in the tumor cells in vivo. Thus, the differential expression of the TC1 gene appears to be related to invasion and metastasis of tumor cells in vivo. The regulation of TC1 gene expression in vivo and in vitro could be a very important model to understand tumorigenesis and tumor malignant behavior.

Expression of TC1 protein

Figure 21A:
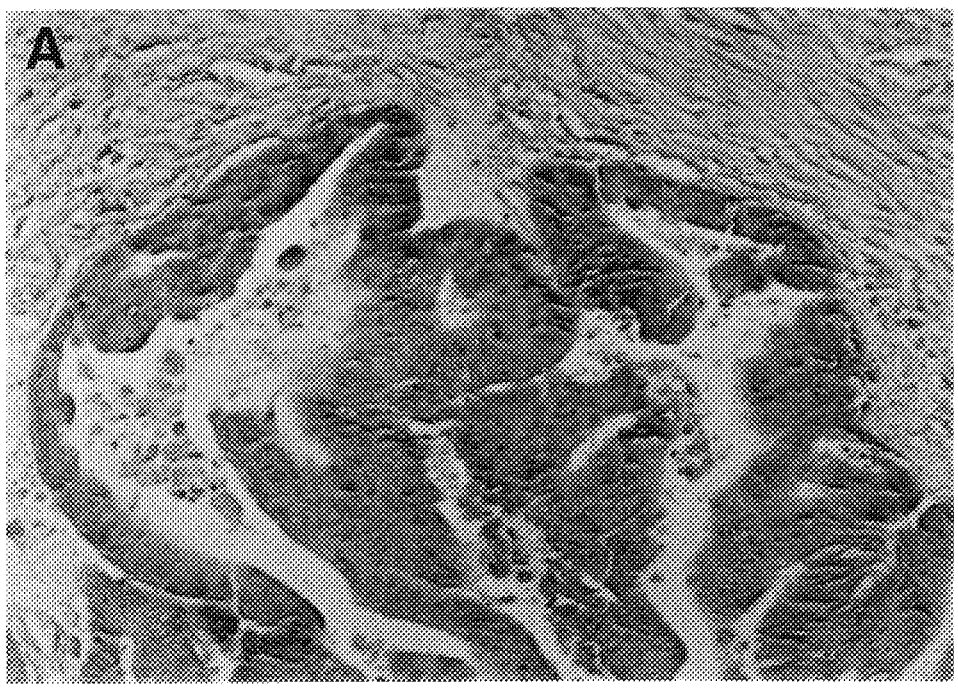
FIGS. 21A–21D show staining of formalin-fixed and paraffin-embedded colon tumor tissue sections using the monoclonal antibody anti-TC1-1 and avidin-biotin-peroxidase detection.
Figure 21B:
Figure 21C:
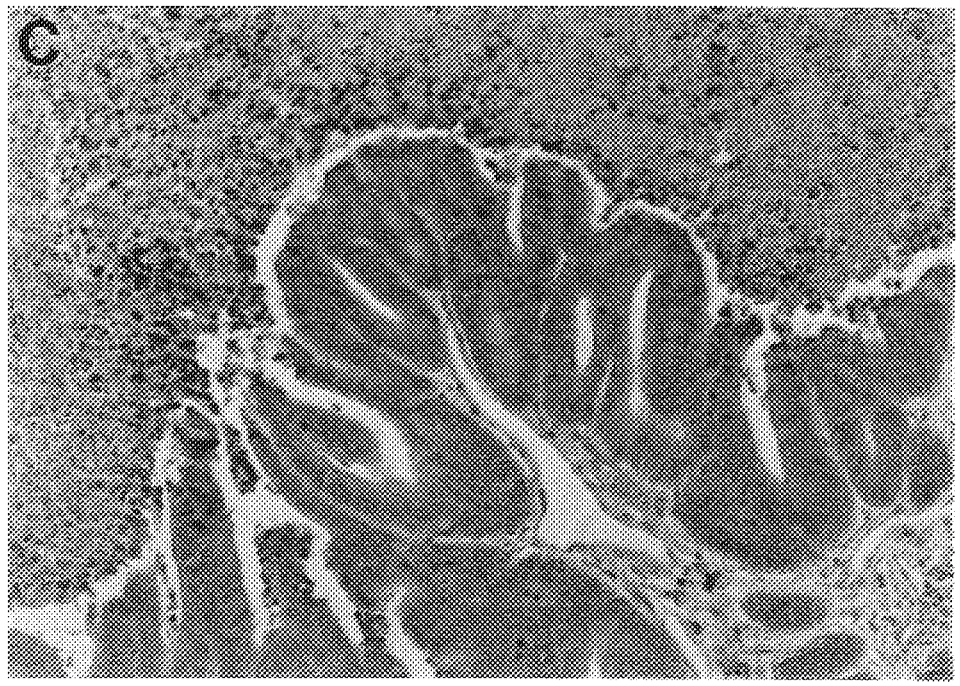
Figure 21D:
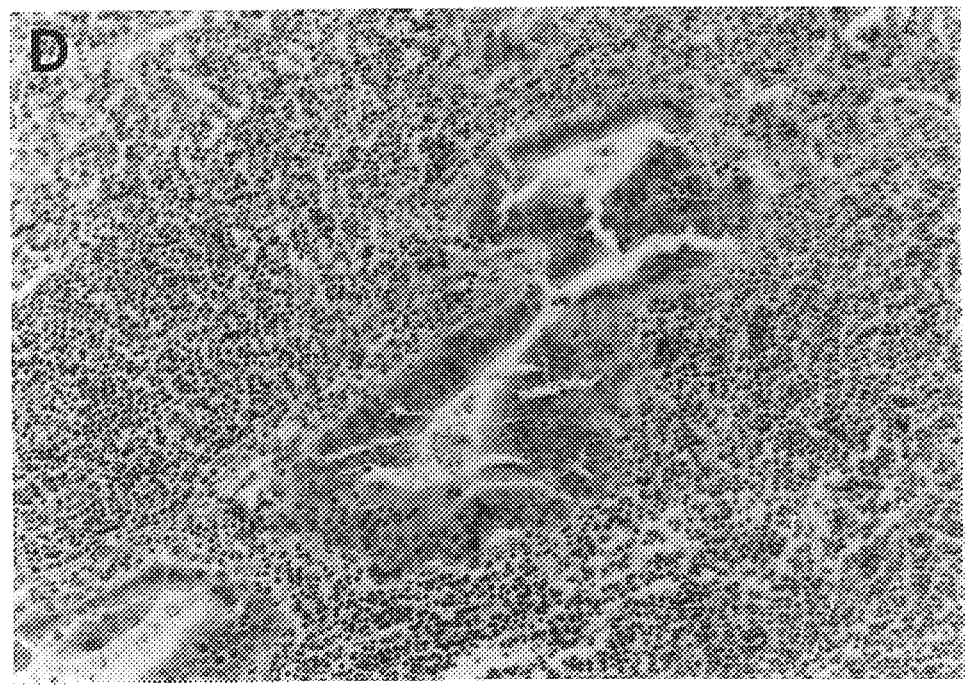
Figure 22A:
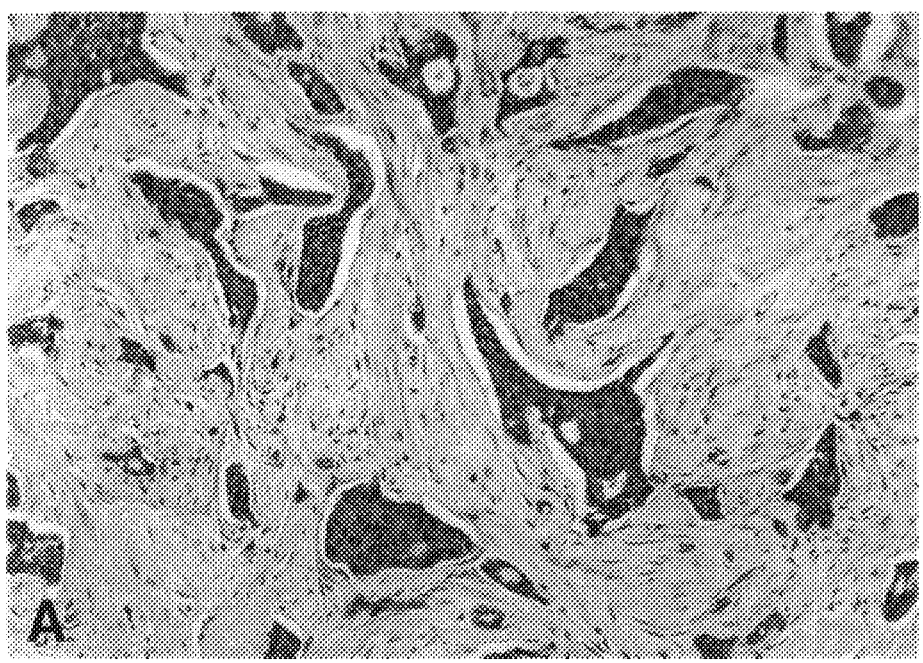
FIGS. 22A–22D show staining as described in FIG. 21, except that panels A, C, D represent breast invasive ductal carcinoma and panel B, normal breast tissue.
Figure 22B:
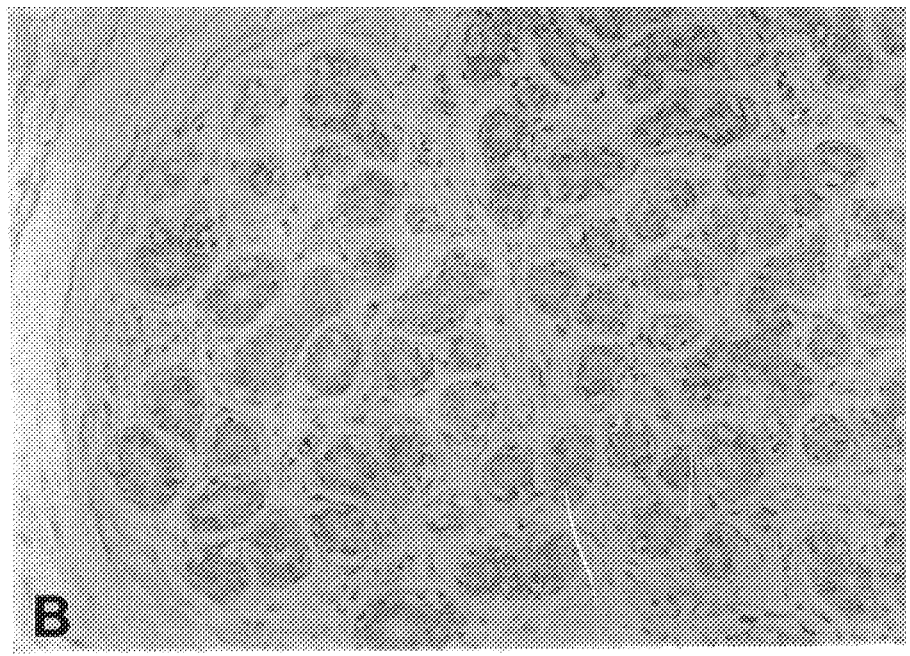
Figure 22C:
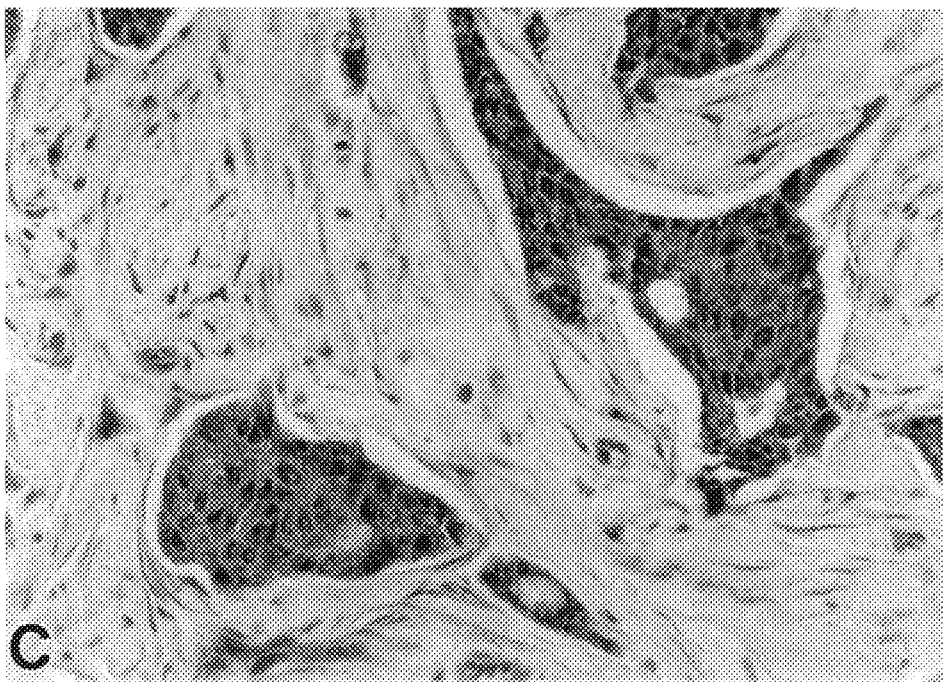
Figure 22D:
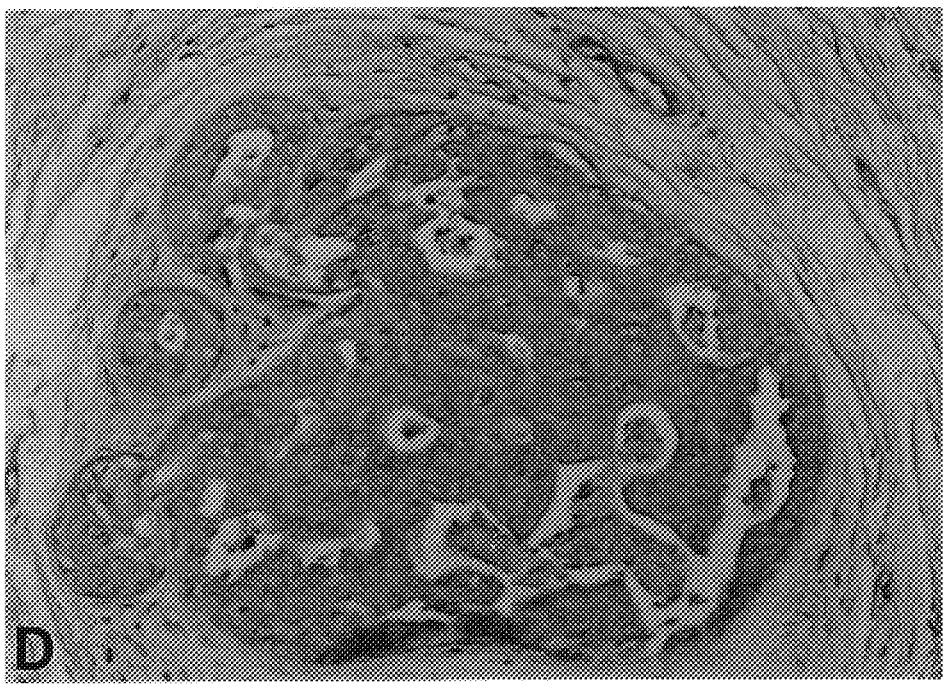
Figure 23A:
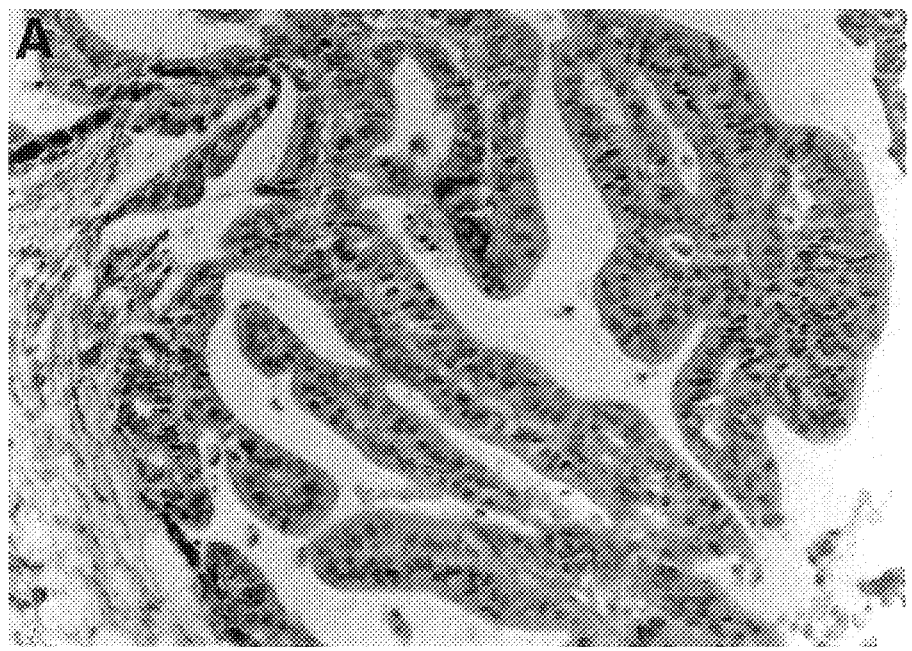
FIGS. 23A–23D show staining as in FIG. 13, except that panels A and B represent gastric carcinoma, and panels C and D, deeply invasive colon carcinoma.
Figure 23B:
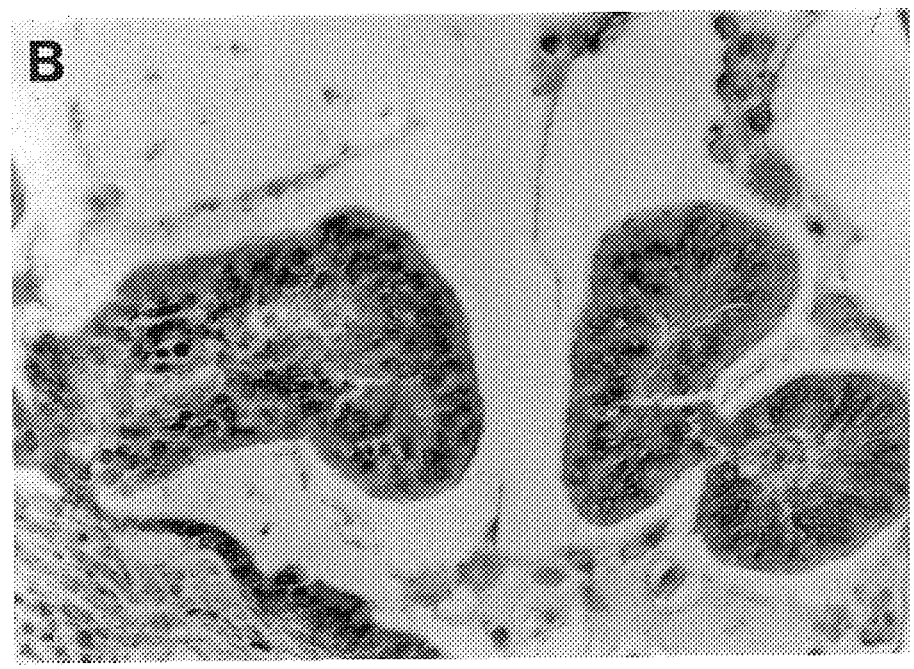
Figure 23C:
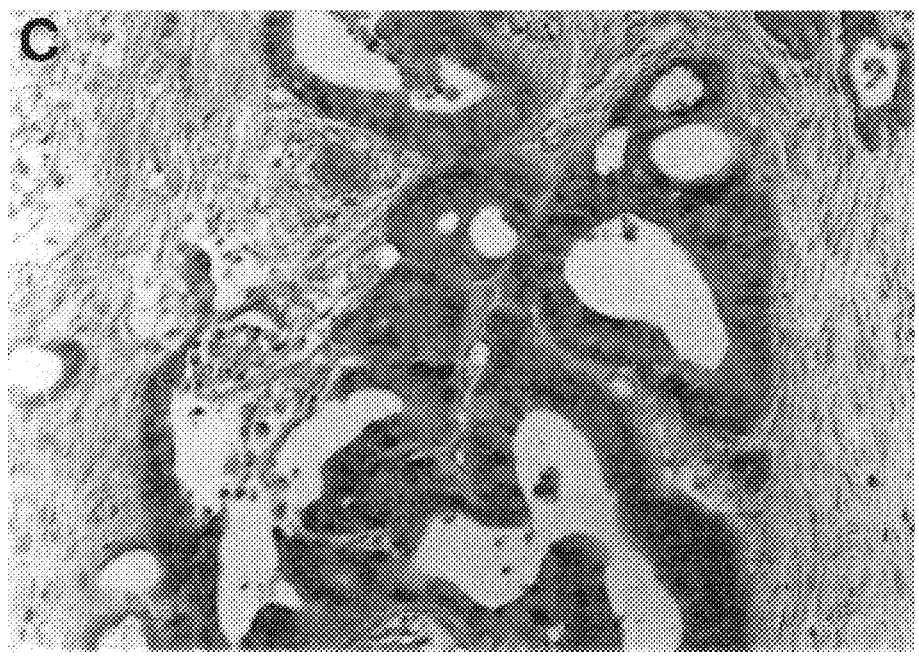
Figure 23D:
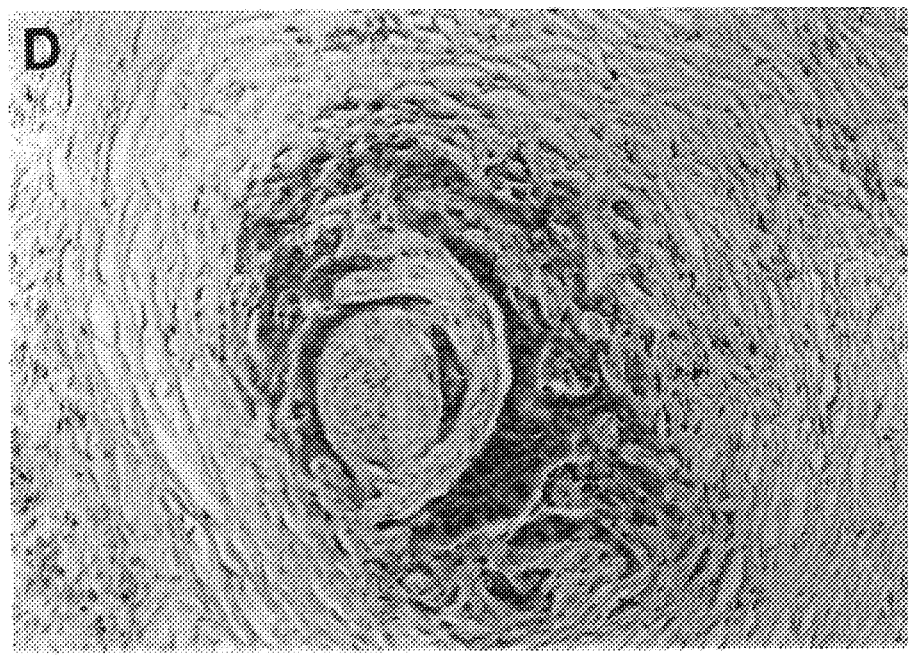

The expression of TC1 protein in in vivo tumor cells, cultured carcinoma cells, and in corresponding normal cells was examined, and is described below. The TC1 gene (SEQ ID NO:3) was cloned into a plasmid expression vector, and recombinant TC1 protein (SEQ ID NO:4) was expressed in bacteria. Several monoclonal antibodies against the bacterially-produced TC1 protein were raised, as will be described below. A variety of formalin-fixed and paraffin-embedded tumor tissue sections were examined by immunohistochemical staining with a mouse monoclonal anti-TC1 antibody anti-TC1-1 using an avidin-biotinylated-peroxidase detection technique. Strong positive staining of TC1 was found in primary colon carcinoma (FIG. 21, panel A), colon carcinoma metastatic to liver (FIG. 21, panel C) and lymph node (FIG. 21, panel D), breast carcinoma (FIG. 22, panels A,C,D) and gastric carcinoma (FIG. 23, panels A,B). The TC1 protein level in tumor tissue is much greater than the level of TC1 in adjacent normal tissue (FIGS. 21B, 23B).

These results, which represent the staining of sixteen cases of different stages of primary colon carcinoma, eight cases of colon tumor metastatic to liver and lymph node, fourteen cases of breast carcinoma and five cases of gastric carcinoma, suggested the following three conclusions. First, the TC1 protein level appeared to be different in different types of carcinoma, with protein levels being highest in breast carcinoma. Second, the advance edge of the deeper invasive tumor appeared stain stronger for TC1, suggesting a greater prevalence of TC1 protein at the advance edge of the tissue. Third, the move advanced stages of tumor appeared to contain more TC1 protein.

Figure 24A:
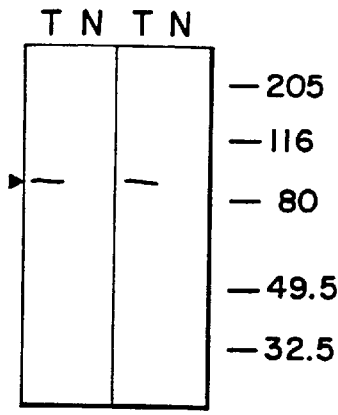
FIGS. 24A and 24B show is a Western Blot analysis of protein samples from two pairs of colon carcinoma and their adjacent normal colon (A) and two pairs of breast carcinoma and their adjacent normal breast (B), using a monoclonal antibody against TC1 protein as a probe.
Figure 24B:
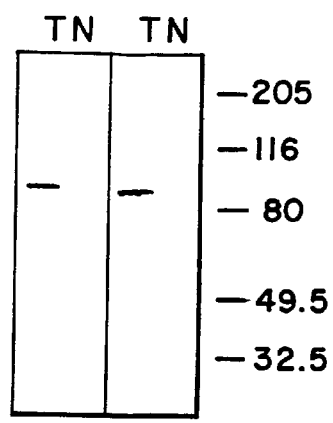

FIG. 24 is a Western Blot analysis of protein samples from two pairs of colon carcinoma and their adjacent normal colon (A) and two pairs of breast carcinoma and their adjacent normal breast (B), using a monoclonal antibody against TC1 protein as a probe. A major 86 kd protein (arrow) was detected by anti-TC1 antibody in tumor samples (T) but not in normal samples (N). The Western Blot analysis confirmed that tumor tissue contained significantly more TC1 protein than the corresponding adjacent normal tissue.

TC1 gene expression

The presence of TC1 mRNA and protein in malignant mesothelioma cells was examined, and is described below.

Figure 25A:
FIG. 25A shows the ethidium bromide staining pattern of an RNA gel in which the same amount of RNA from JMN (1) and JMN1B (2) cells is loaded per lane.
Figure 25B:
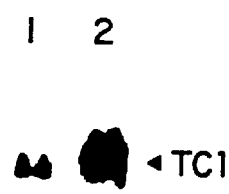
FIG. 25B is a Northern Blot analysis of RNA from malignant mesothelioma cells JMN1B (2) and JMN (1) using TC1 cDNA as a probe.

More than 42 cell lines have been screened for TC1 gene expression by Northern Blot analysis. However, only two cell lines, JMN1B and JMN, express detectable mRNA by Northern Blot analysis. JMN1B and JMN are malignant mesothelioma, JMN1B being a subline of JMN cells with showing enhanced tumorigenicity after passage of JMN cells through a nude mouse. FIG. 25 is a Northern Blot analysis of RNA from malignant mesothelioma cells JMN1B and JMN using TC1 cDNA as a probe. The results presented in Panel 25B demonstrate that TC1 mRNA level in JMN1B cells (2) is much greater than that in JMN cells (1). Panel 25A shows the ethidium bromide staining pattern of an RNA gel in which the same amount of JMN (1) and JMN1B (2) RNA is loaded per lane.

The Northern Blot analysis revealed that the TC1 mRNA level is much higher in JMN1B than in JMN, the JMN1B/JMN ratio being approximately 14. Higher expression of TC1 mRNA in JMN1B could be related to the observed greater tumorigenicity of JMN1B cells. It has been found that JMN1B cells can secrete an "EGF-like" growth factor called transformed mesothelial growth factor (TMGF) that satisfies the EGF requirement of normal human mesothelial cells. The difference in the levels of TC1 mRNA in JMN1B and JMN cells provides an ideal cell model to understand the regulation of TC1 expression and its relation to tumorigenicity.

Figure 26:
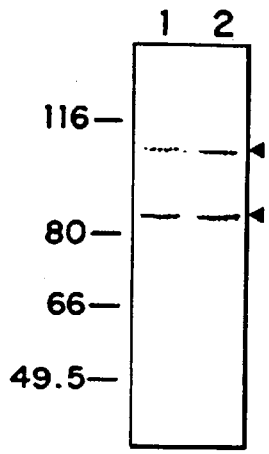
FIG. 26 is a Western blot using a monoclonal antibody against TC1 to probe JMN1B cells grown in conditioned medium and whole cell lysate.
Figure 27A:
FIGS. 27A–27D show JMN1B cells fixed with paraformaldehyde without subsequent permeabilization in panels A and B, and JMN1B cells fixed with paraformaldehyde and then permeabilized in panels C and D.
Figure 27B:
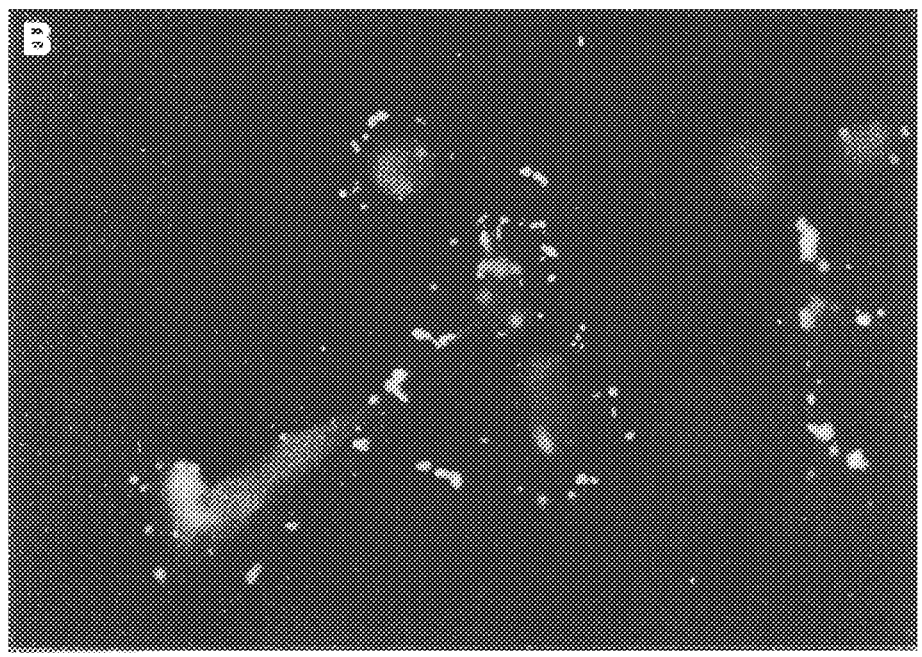
Figure 27C:
Figure 27D:

Sequence analysis of the deduced amino acid sequence has revealed that the TC1 protein (SEQ ID NO:4) contained a secretory leader signal at its N-terminus. The secretion of TC1 protein was confirmed by Western Blot analysis of conditioned medium of JMN1B cells. JMN1B cells were cultured in regular medium until 90% confluent, then cultured in serum free medium for two days. This serum free conditioned medium was analyzed by immunoblotting with anti-TC1 monoclonal antibody. FIG. 26 is a Western blot analysis using a monoclonal antibody against TC1 to probe JMN1B cells grown in conditioned medium and whole cell lysate. Two major bands (about 86 kd and 104 kd) were recognized by anti-TC1 antibody both in JMN1B cell conditioned medium (1) and whole cell lysate (2). Numbers on the left indicate the position of molecular weight standards in kilodalton. The protein size of the lower molecular weight 86 kd band is consistent with that of deduced TC1 protein, whereas the higher molecular weight 104 kd band is consistent with a TC1 glycoprotein. There is one predicted site of N-linked glycosylation at the amino acid residue 605 (NDT) of deduced TC1 protein sequence. There are 60 threonine residues and 36 serine residues in the deduced TC1 sequence, each of which is a potential site of O-linked glycosylation.

Human malignant mesothelioma cell line JMN1B can express abundant TC1. This cell line was used to study the distribution and localization of TC1 protein by immunofluorescent staining with an anti-TC1 monoclonal antibody followed by Rhodamine conjugated goat anti-mouse IgG secondary antibody. When JMN1B cells were fixed with paraformaldehyde without subsequent permeabilization, the positive staining was seen on the cell surface or outside of the cell (FIG. 27, panels A,B), which confirms the secretion of TC1 protein. When JMN1B cells were fixed with paraformaldehyde and then permeabilized, positive staining appeared in the Golgi complex and the endoplasmic reticulum (ER) in the cell (FIG. 27, panels C,D), suggesting that TC1 protein is synthesized in the ER and Golgi complex. The staining in the Golgi complex is clearly evident, indicating that glycosylation of TC1 protein may be located in the Golgi complex. The TC1 protein distribution pattern also suggests that TC1 is a secreted glycoprotein.

Without being bound to one theory as to the biological function of TC1, observations as to the prevalence and expression of TC1 mRNA and protein indicate that TC1 may be related to tumor malignant behavior such as invasion and metastases. These observations include the following: TC1 is significantly overexpressed in tumor tissue; TC1 is a secreted protein; later stage tumor expresses higher levels of TC1; deeper invasive tumor contains higher levels of TC1 protein; TC1 expression turns off in cultured tumor cells in vitro and turns on again after cells grow tumor tissue in vivo. These observations indicate that the function of TC1 is not related to tumor cell proliferation, but is more likely involved in tumor malignant behavior in vivo, such as invasion and metastases.

TC1 is a member of a Family of Proteins

Figure 8:
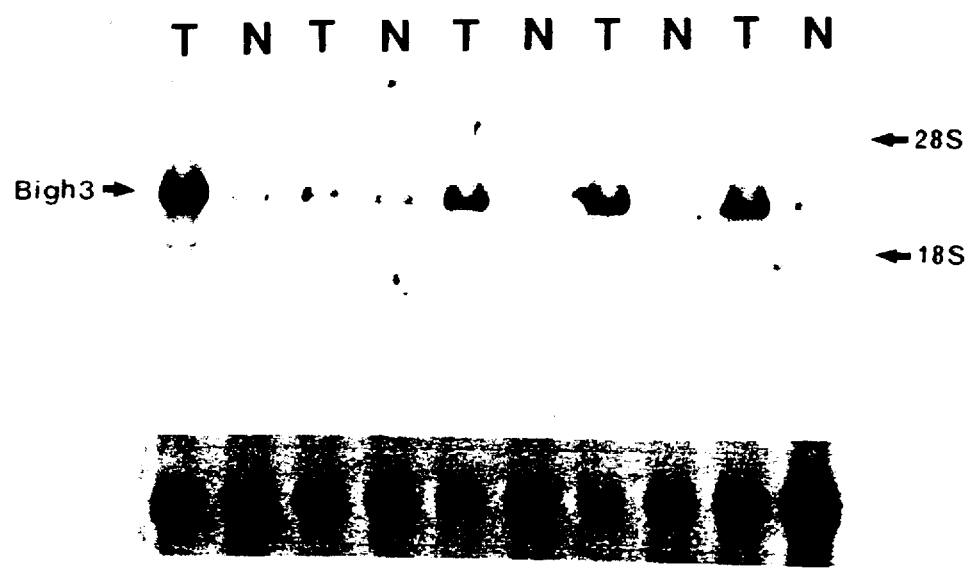
FIG. 8 is a Northern Blot of five pairs of RNA from colon carcinoma (T) and adjacent normal colon tissue (N) probed with 32P-labeled Big-h3 cDNA, the bottom panel representing control RNA probed with 32P-labeled B-actin.

A FASTA search of the GenBank and EMBL database with the TC1 open reading frame indicated that the protein is unique. However, TC1 whole protein shared 45% sequence identity with a TGF-beta inducible gene, Big-h3, at the amino acid level, suggesting that TC1 and Big-h3 may belong to a new gene family. The identity between TC1 (SEQ ID NO:4) and Big-h3 (SEQ ID NO:11) at the amino acid level is shown in FIG. 7. In FIG. 7, identical amino acids between TC1 and Big-h3 are boxed. Several stretches of amino acids are highly conserved between TC1 and Big-h3. Northern Blot analysis showed that the TC1 gene is expressed from a larger transcript than Big-h3, and DNA sequence analysis indicated that TC1 contains a longer open reading frame encoding a higher molecular weight protein than the Big-h3 gene. It has been found that Big-h3 also contains four internal repeats. The amino acid sequence homology and structural similarity between TC1 and Big-h3 indicate their functional similarity and relationship. We found that Big-h3 mRNA is also much more abundant in colon carcinoma tissue than in adjacent normal colon tissue (FIG. 7). FIG. 8 is a Northern Blot of five pairs of RNA from colon carcinoma (T) and adjacent normal colon tissue (N) probed with $^{32}$P-labeled Big-h3 cDNA. The blot shows Big-h3 mRNA level in colon carcinoma to be much higher than that in adjacent normal tissue. The bottom panel represents control RNA probed with $^{32}$P-labeled B-actin.

In contrast to the expression pattern of TC1 mRNA, which is shown to be largely restricted to in vivo tumor tissue, Big-h3 mRNA is not only expressed in the tumor tissue, but also expressed in the cultured tumor cell lines and some normal cell lines. Though TC1 and Big-h3 shared significant homology, their responses to growth factors are distinctly different.

Fasciclin I, II, III are extrinsic membrane glycoproteins involved in the growth cone guidance during nervous system development in the insect embryo. A search of NBRF protein database revealed a significant homologous domain between TC1 and Fasciclin I from Grasshopper and Drosophila. One TC1 domain of 204 amino acids (amino acid residue 503–706) shared 30% identity with Grasshopper Fasciclin I, and shared 25% identity with Drosophila Fasciclin. FIG. 9 shows amino acid sequence homology between TC1 (SEQ ID NO:4) and Fasciclin I from Grasshopper (GrF) (SEQ ID NO:18) and Drosophila (DrF) (SEQ ID NO:19). Boxed amino acids are identical with at least one other amino acid at that same position.

It has been found that Fasciclin also contained four internal homologous domains, each consisting of approximately 150 amino acids. The domains of TC1 and Fasciclin I share some highly conserved amino acid stretches which appear to include important motifs of this gene family.

Screening for antagonists to TC1 function

The invention also includes methods of screening for agents which inhibit TC1 gene expression, whether such inhibition be at the transcriptional or translational level.

Screening methods, according to the invention, for agents which inhibit expression of the TC1 gene in vitro will include exposing a metastatic cell line in which TC1 mRNA is detectable in culture to an agent suspected of inhibiting production of the TC1 mRNA; and determining the level of TC1 mRNA in the exposed cell line, wherein a decrease in the level of TC1 mRNA after exposure of the cell line to the agent is indicative of inhibition of TC1 mRNA production.

Alternatively, such screening methods may include in vitro screening of a metastatic cell line in which TC1 protein is detectable in culture to an agent suspected of inhibiting production of the TC1 protein; and determining the level of TC1 protein in the cell line, wherein a decrease in the level of TC1 protein after exposure of the cell line to the agent is indicative of inhibition of TC1 protein production.

The invention also encompasses in vivo methods of screening for agents which inhibit expression of the TC1 gene, comprising exposing a mammal having tumor cells in which TC1 mRNA or protein is detectable to an agent suspected of inhibiting production of TC1 mRNA or protein; and determining the level of TC1 mRNA or protein in tumor cells of the exposed mammal. A decrease in the level of TC1 mRNA or protein after exposure of the mammal to the agent is indicative of inhibition of TC1 gene expression.

According to the invention, agents can be screened in vitro or in vivo as follows. For in vitro screening, a metastatic cell line, e.g., JMN1B, may be cultured in vitro and exposed to an agent suspected of inhibiting TC1 expression in an amount and for a time sufficient to inhibit such expression. For in vivo screening, a mammal afflicted with a late stage cancer, particularly one of breast cancer, colon cancer, or cancer of the gastrointestinal tract, is exposed to the agent at a dosage and for a time sufficient to inhibit expression of TC1. A late stage cancer is defined by the Duke's stage of the cancer; i.e., late stage cancers correspond to Duke's stages 3–4. The amount or dosage of the agent which is effective to inhibit TC1 expression may be determined using serial dilutions of the agent. The level of TC1 mRNA or protein may be determined using an aliquot of cells from the cell culture or the in vivo tumor and performing Northern Blot analysis or Western Blot analysis, respectively. The agent will be considered inhibitory if the level of TC1 mRNA or protein decreases by more than 50%, and preferably more than 70–80%, relative to the same cell line which has not been exposed to the agent.

Examples of potential inhibitors of TC1 mRNA or protein production include but are not limited to antisense RNA, competitive inhibitors of the TC1 protein such as fragments of the TC1 protein itself, or antibodies to TC1 protein. Candidate TC1 inhibitory fragments include, but are not limited to, SEQ ID NO:4, amino acid residues 276–285 and amino acid residues 361–368.

Use of antagonists to TC1 functions

The invention also encompasses the treatment of late stage cancers by administration to a mammal afflicted with a late stage cancer one or more of the above-selected inhibitory agents. Late stage cancers, particularly those of the breast, colon, or gastrointestinal tract, are treated according to the invention by administering the inhibitory agent to a mammal afflicted with a late stage cancer in an amount and for a time sufficient to decrease the level of TC1 protein or mRNA.

The mode of administration may be intravenously, intraperitoneally, by intramuscular or intradermal injection, or orally. Administration may be by single dose, or may be continuous or intermittent. The dosage of inhibitory agent is that dosage which is effective to inhibit TC1 production, i.e., within the range of 10 µg/kg body weight—100 gm/kg body weight, preferably, within the range of 1 mg/kg body weight—1 gm/kg body weight, most preferably 10–100 mg/kg body weight.

Production of monoclonal antibodies reactive with TC1

An anti-TC1 antibody is produced according to Kohler and Milstein, Nature, 256:495–497 (1975), Eur. J. Immunol. 6:511–519 (1976), both of which are hereby incorporated by reference, using the TC1 protein or a fragment thereof as the immunizing antigen. Hybridomas produced by the above process are selected for anti-TC1 antibodies using the TC1 as an antigen in an ELISA assay. The single type of immunoglobulin produced by a such a hybridoma is specific for a single antigenic determinant, or epitope, on the TC1 antigen. Certain TC1-specific antibodies, for example, anti-TC1-1 produced by the hybridoma deposited with the American Type Culture Collection (ATCC) under the ATCC number HB 11481, are unique in that they recognize the TC1 protein, more specifically an epitope of the TC1 protein, in formaldehyde-fixed and paraffin-embedded tumor cells which bear TC1.

Deposits

The following samples were deposited on Oct. 29, 1993, with the American Type Culture Collection (ATCC), 10801University Boulevard, Manassas, Va. 20110-2209.

| Deposit | ATCC Accession No. |
| --- | --- |
| TC1 gene in pBluescript plasmid DNA vector | 75599 |
| Hybridoma TC-1 | HB 11481 |

Applicants' assignee, Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1,14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

OTHER EMBODIMENTS

The invention is not limited to those embodiments described herein, but may encompass modifications and variations which do not depart from the spirit of the invention. While the invention has been described in connection with specific embodiments thereof, it will be understood that further modifications are within the scope of the following claims.

What is claimed is:

1. A monoclonal antibody that binds to an epitope of tumor marker protein TC1, said protein having the amino acid sequence of SEQ ID NO:4, in formalin-fixed or paraffin-embedded tissues.

2. A monoclonal antibody produced by the hybridoma cell line ATCC No. HB 11481, or a monoclonal antibody that binds to the same antigenic determinant as a monoclonal antibody produced by the hybridoma cell line ATCC No. HB 11481.

3. A method for detecting a tumor in a subject comprising the steps of:

providing a sample of body fluid or a sample of a tissue section from said subject;

contacting said sample with a monoclonal antibody specific for an epitope of tumor marker protein TC1 having the amino acid sequence of SEQ ID NO:4; and determining the extent of binding of said monoclonal antibody to said sample, wherein said extent of binding is indicative of the level of said TC1 protein in said sample, and wherein further the presence of said TC1 protein in said sample is indicative of the presence of a tumor in said subject.

4. The method of claim 3, wherein said body fluid is selected from the group consisting of blood, urine and sputum.

5. A method for detecting an invasive or metastatic tumor comprising the steps of:

providing a sample of a formalin-fixed or paraffin-embedded tissue section from said subject;

contacting said sample with a monoclonal antibody specific for an epitope of tumor marker protein TC1, said protein having the amino acid sequence of SEQ ID NO:4; and determining the extent of binding of said monoclonal antibody to said sample, wherein said extent of binding is indicative of the level of said TC1 protein in said sample, and wherein further the presence of said TC1 protein in said sample is indicative of the presence of an invasive or metastatic tumor in said subject.

6. The method of claim 3 or 5, wherein said tissue is breast, colon, or gastrointestinal tract tissue.

7. The method of claim 5, wherein said monoclonal antibody is a monoclonal antibody produced by the hybridoma cell line ATCC No. HB 11481.

8. The method of claim 5, wherein said monoclonal antibody is a monoclonal antibody that binds to the same antigenic determinant as a monoclonal antibody produced by the hybridoma cell line ATCC No. HB 11481.

9. A kit for diagnosis of an invasive or metastatic tumor in a subject, comprising the monoclonal antibody of claim 1 or claim 2.

* * * * *